US012667366B2

(12) United States Patent
Jackson et al.

(10) Patent No.: US 12,667,366 B2
(45) Date of Patent: Jun. 30, 2026

(54) HIGH-PRESSURE EMBOLIC MATERIAL DELIVERY DEVICE AND RELATED TECHNOLOGY

(71) Applicant: Covidien LP, Mansfield, MA (US)

(72) Inventors: Brad L. Jackson, San Diego, CA (US); Edwin Y. Wang, Tustin, CA (US); Maria D. Sanson, Mission Viejo, CA (US); Sotheany Seang, Garden Grove, CA (US); Sydney L. Ngo, Riverside, CA (US); Komonn Lim, Lake Forest, CA (US); Mehdi M. Rashidi, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 251 days.

(21) Appl. No.: 18/060,719

(22) Filed: Dec. 1, 2022

(65) Prior Publication Data

US 2024/0180561 A1 Jun. 6, 2024

(51) Int. Cl.
*A61B 17/12* (2006.01)

(52) U.S. Cl.
CPC .. *A61B 17/12177* (2013.01); *A61B 17/12036* (2013.01); *A61B 17/12113* (2013.01)

(58) Field of Classification Search
CPC ........ A61B 17/12177; A61B 17/12036; A61B 17/12113; A61B 17/12186; A61M 25/0138; A61M 25/0051; A61M 2025/0681; A61M 2025/0175
See application file for complete search history.

(56) References Cited

U.S. PATENT DOCUMENTS

| | | | |
|---|---|---|---|
| 8,468,919 | B2 | 6/2013 | Christian et al. |
| 9,067,332 | B2 | 6/2015 | Lippert et al. |
| 9,067,333 | B2 | 6/2015 | Lippert et al. |
| 9,072,873 | B2 | 7/2015 | Lippert et al. |
| 9,950,137 | B2 | 4/2018 | Lippert et al. |
| 10,363,389 | B2 | 7/2019 | Lippert et al. |
| 11,369,351 | B2 | 6/2022 | Davis et al. |
| 11,406,791 | B2 | 8/2022 | Lippert et al. |
| 2003/0023190 | A1 | 1/2003 | Cox |

(Continued)

FOREIGN PATENT DOCUMENTS

| | | |
|---|---|---|
| WO | 2020252506 A1 | 12/2020 |

*Primary Examiner* — Darwin P Erezo
*Assistant Examiner* — Raihan R Khandker
(74) *Attorney, Agent, or Firm* — Fortem IP LLP

(57) ABSTRACT

An embolic material delivery device in accordance with at least some embodiments of the present technology achieves a high pressure rating with a small wall thickness. The device includes an elongate conduit body configured to extend intravascularly toward a treatment location including an aneurysm. The conduit body defines an axial lumen through which viscous embolic material is conveyed toward the aneurysm while at least a portion of the liquid embolic material is at very high pressure (e.g., 9,000 psi or greater). The conduit body includes a metal hypotube coaxially disposed around the axial lumen. The hypotube includes cuts configured to increase a flexibility of the conduit body and bridges between the cuts. The conduit body further includes an elastomeric jacket extending around at least a portion of the hypotube. An average wall thickness of the conduit body is within a range of 0.005 to 0.007 inches.

13 Claims, 12 Drawing Sheets

(56)  References Cited

U.S. PATENT DOCUMENTS

| | | | |
|---|---|---|---|
| 2003/0093059 A1* | 5/2003 | Griffin | A61M 25/0045 |
| | | | 604/525 |
| 2004/0153049 A1 | 8/2004 | Hewitt et al. | |
| 2004/0181174 A2 | 9/2004 | Davis et al. | |
| 2005/0256508 A1* | 11/2005 | Hall | A61M 25/0668 |
| | | | 604/529 |
| 2006/0121218 A1 | 6/2006 | Obara et al. | |
| 2007/0135763 A1 | 6/2007 | Musbach et al. | |
| 2007/0167876 A1 | 7/2007 | Euteneuer et al. | |
| 2008/0200839 A1 | 8/2008 | Bunch et al. | |
| 2015/0374955 A1 | 12/2015 | Hebert | |
| 2017/0079662 A1* | 3/2017 | Rhee | A61B 17/12177 |
| 2019/0175874 A1* | 6/2019 | Tada | A61M 25/0013 |
| 2020/0077991 A1* | 3/2020 | Gordon | A61B 17/3478 |
| 2020/0230359 A1* | 7/2020 | Fojtik | A61M 25/0013 |
| 2021/0213241 A1 | 7/2021 | Christian et al. | |
| 2021/0213243 A1 | 7/2021 | Guo et al. | |
| 2024/0407772 A1* | 12/2024 | Gafford | A61M 25/0138 |

* cited by examiner

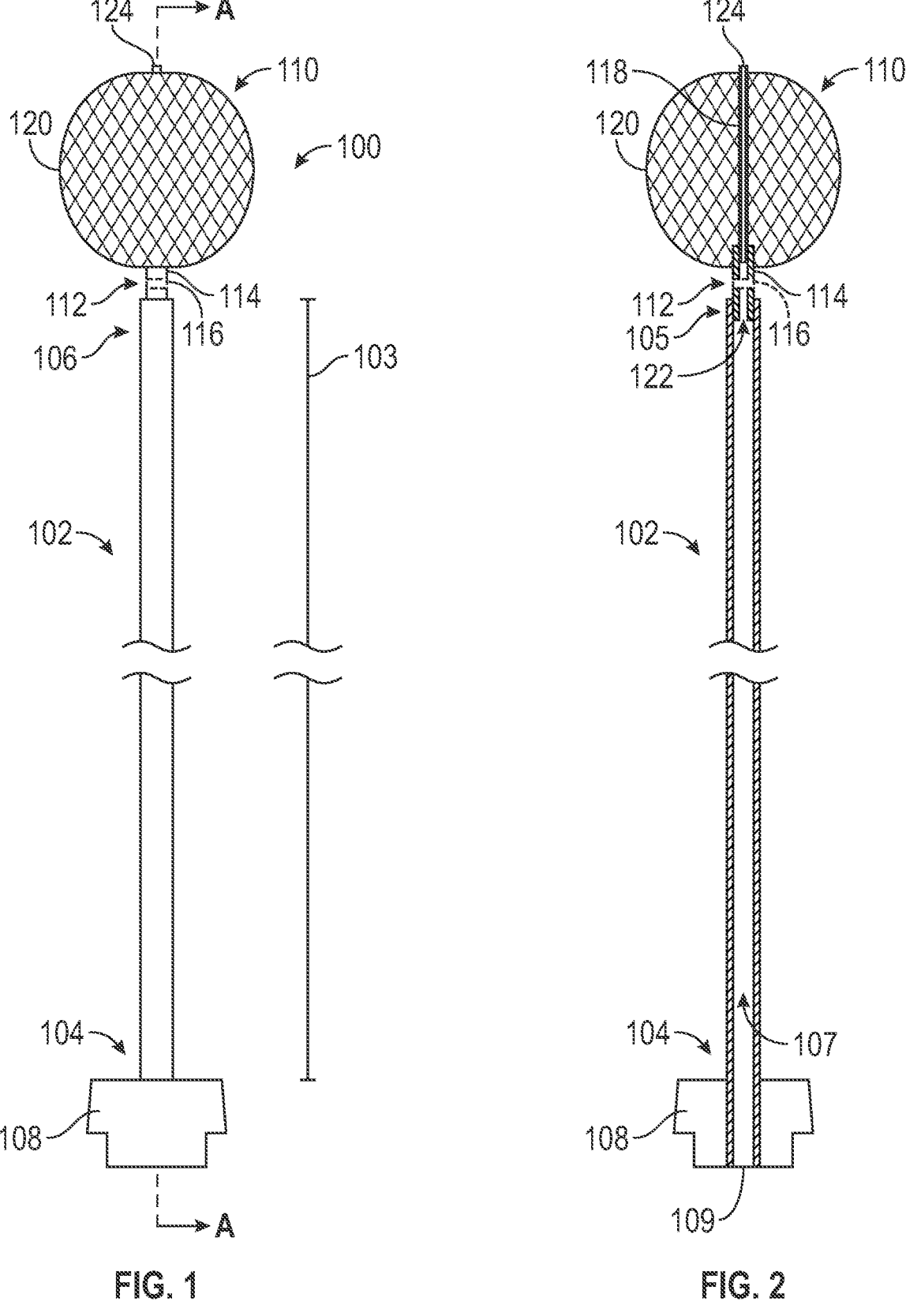
FIG. 1                                    FIG. 2

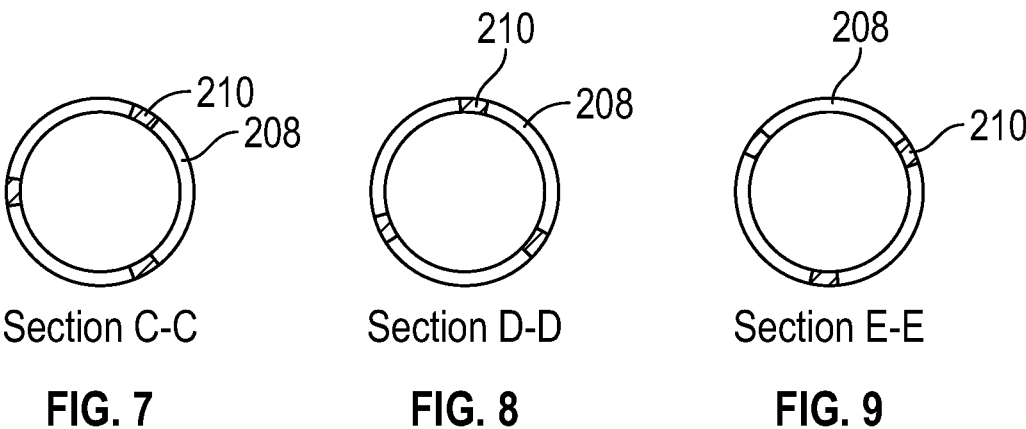
Section C-C
FIG. 7
Section D-D
FIG. 8
Section E-E
FIG. 9
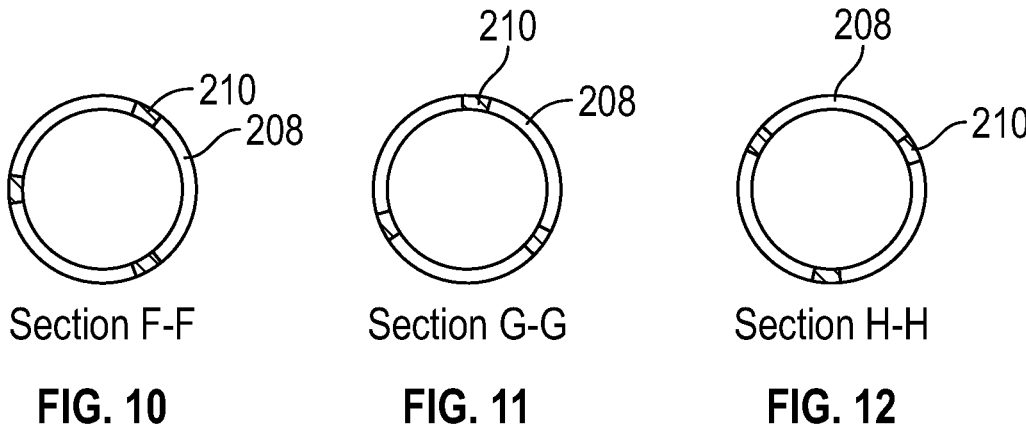
Section F-F
FIG. 10
Section G-G
FIG. 11
Section H-H
FIG. 12
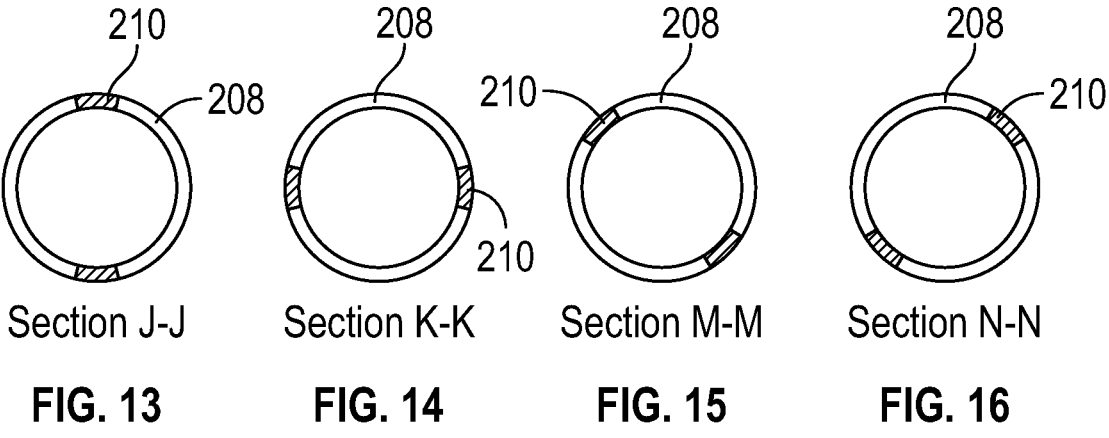
Section J-J
FIG. 13
Section K-K
FIG. 14
Section M-M
FIG. 15
Section N-N
FIG. 16

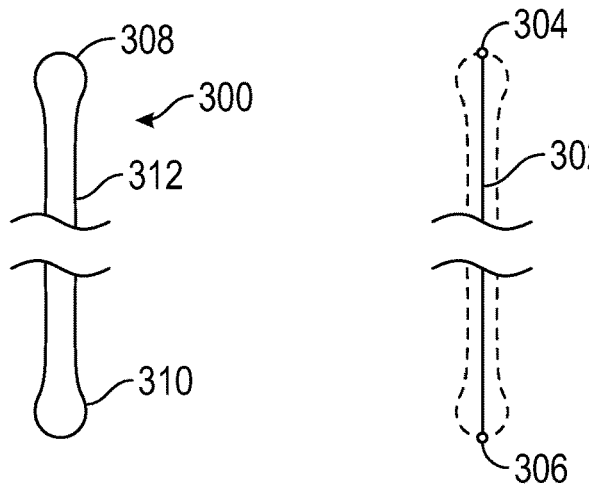
FIG. 17A          FIG. 17B
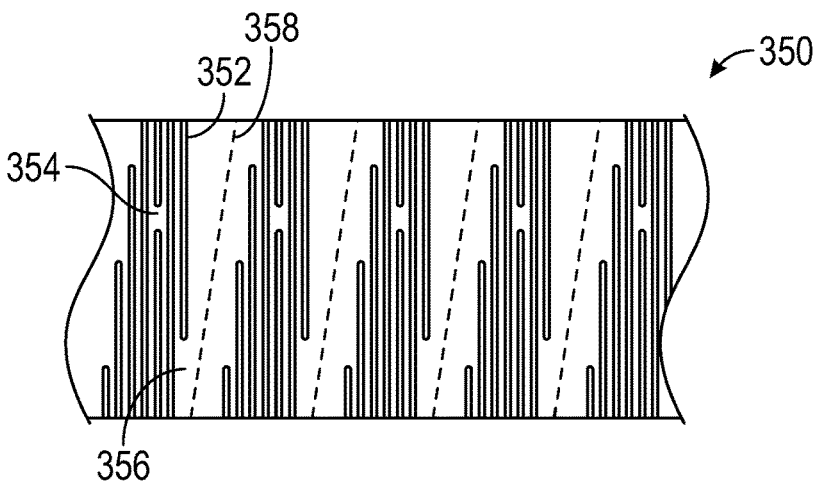
FIG. 18
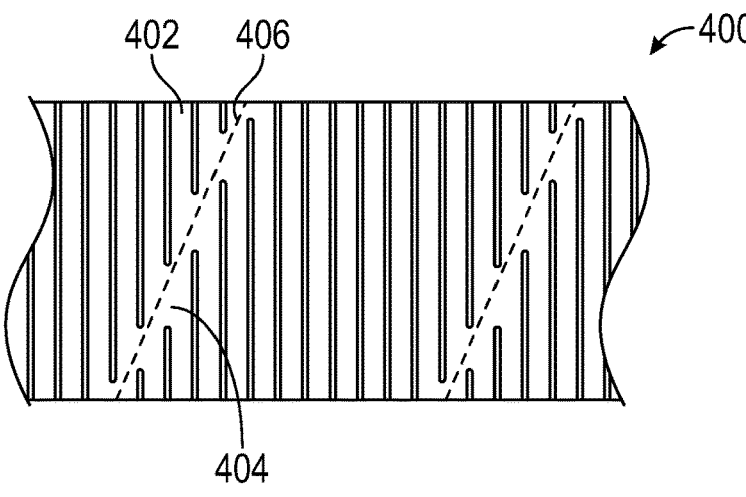
FIG. 19

HIGH-PRESSURE EMBOLIC MATERIAL DELIVERY DEVICE AND RELATED TECHNOLOGY

TECHNICAL FIELD

The present technology relates to devices for moving embolic material toward treatment locations within the human body, such as in the context of treating aneurysms.

BACKGROUND

An aneurysm is an abnormal bulging or ballooning at a weakening in a wall of a blood vessel. Causes of aneurysms include disease, injury, and congenital abnormality. Although aneurysms can occur in many different parts of the body, the most common locations are the aorta and the intracranial vasculature. It is estimated that 2% or more of the worldwide population harbors an unruptured intracranial aneurysm. Many of these intracranial aneurysms eventually rupture leading to severe complications, such as subarachnoid hemorrhage. Unfortunately, the prognosis for subarachnoid hemorrhage is poor. Most patients with this condition either die or suffer from long-term cognitive impairment. The probability of death or disability from a ruptured aortic aneurysm can be even higher than from a ruptured intracranial aneurysm. Fortunately, treatments for ruptured and unruptured aneurysms currently exist and continue to improve. Many of these treatments involve reducing blood flow within an aneurysm and thereby promoting thrombosis and embolization. Aneurysms treated in this manner are significantly less likely to rupture and/or hemorrhage than if left untreated. These and other treatments have the potential to save thousands of lives every year. Accordingly, there is an ongoing public health need for inventive effort in this field.

SUMMARY

An embolic material delivery device in accordance with at least some embodiments of the present technology includes a conduit body configured to extend intravascularly toward a treatment location. The conduit body is elongate, defines an axial lumen, and comprises a proximal end portion and a distal end portion opposite to the proximal end portion along a length of the conduit body. The axial lumen extends between the proximal and distal end portions of the conduit body. The conduit body further comprises a hypotube coaxially disposed around the axial lumen. The hypotube includes cuts configured to increase a flexibility of the conduit body. The conduit body still further comprises an elastomeric jacket extending around at least a portion of the hypotube. The conduit body is configured to convey liquid embolic material toward the treatment location via the axial lumen while at least a portion of the liquid embolic material is at a pressure of 9,000 psi or greater.

A method for treating an aneurysm at a neurovascular treatment location in accordance with at least some embodiments of the present technology includes moving a distal end portion of a conduit body intravascularly toward the neurovascular treatment location. The method further includes bending the conduit body while moving the distal end portion of the conduit body intravascularly toward the neurovascular treatment location. Bending the conduit body includes at least partially collapsing first cut regions of a hypotube of the conduit body and expanding second cut regions of the hypotube. The first and second cut regions are circumferentially opposite to one another around a length of the conduit body. The method further includes flowing liquid embolic material distally toward the aneurysm via the axial lumen after bending the conduit body and while at least a portion of the liquid embolic material is at a pressure of 9,000 psi or greater.

Examples of aspects of the present technology are described below as numbered clauses (1, 2, 3, etc.) for convenience. These are provided as examples and do not limit the present technology.

Clause 1. An embolic material delivery device, comprising:
a conduit body configured to extend intravascularly toward a treatment location, wherein the conduit body is elongate, defines an axial lumen, and comprises:
a proximal end portion,
a distal end portion opposite to the proximal end portion along a length of the conduit body, wherein the axial lumen extends between the proximal and distal end portions of the conduit body,
a hypotube coaxially disposed around the axial lumen, wherein the hypotube includes cuts configured to increase a flexibility of the conduit body, and
a jacket extending around at least a portion of the hypotube, wherein the jacket is elastomeric,
wherein the conduit body is configured to convey liquid embolic material toward the treatment location via the axial lumen while at least a portion of the liquid embolic material is at a pressure of 9,000 psi or greater.

Clause 2. The embolic material delivery device of any of the preceding or following clauses, wherein the cuts are laser cuts.

Clause 3. The embolic material delivery device of any of the preceding or following clauses, wherein the conduit body defines an average wall thickness within a range of 0.004 to 0.008 inches.

Clause 4. The embolic material delivery device of any of the preceding or following clauses, wherein the conduit body defines an average wall thickness within a range of 0.005 to 0.007 inches.

Clause 5. The embolic material delivery device of any of the preceding or following clauses, wherein the jacket defines an average durometer within a range of 20D to 90 D.

Clause 6. The embolic material delivery device of any of the preceding or following clauses, wherein the jacket extends at least partially into the cuts.

Clause 7. The embolic material delivery device of any of the preceding or following clauses, wherein a composition of the jacket at a distalmost portion of the conduit body is different than a composition of the jacket at a next distalmost portion of the conduit body.

Clause 8. The embolic material delivery device of any of the preceding or following clauses, wherein the hypotube comprises stainless steel, nitinol, polyether ether ketone, or a combination thereof.

Clause 9. The embolic material delivery device of any of the preceding or following clauses, wherein the jacket comprises polyurethane, poly(ether-amide), nylon, or a combination thereof.

Clause 10. The embolic material delivery device of any of the preceding or following clauses, wherein an average wall thickness of the jacket excluding any portions of the jacket extending into the cuts is no more than 110% of an average wall thickness of the hypotube excluding the cuts.

Clause 11. The embolic material delivery device of any of the preceding or following clauses, wherein:

the cuts individually define a cut length and a cut width perpendicular to the cut length; and an average of the cut widths is within a range of 0.028 to 0.043 mm.

Clause 12. The embolic material delivery device of any of the preceding or following clauses, wherein:

the cuts individually define a cut length and a cut width perpendicular to the cut length; and a ratio of an average of the cut widths to an average of the cut lengths is within a range of 0.020:1 to 0.028:1.

Clause 13. The embolic material delivery device of any of the preceding or following clauses, wherein:

the cuts individually define a cut length and a cut width perpendicular to the cut length;

the cuts individually include:

a first end portion at a first end of the cut length, a second end portion at a second end of the cut length opposite to the first end of the cut length, and an intermediate portion between the first and second end portions; and an average of the cut widths at the first and second end portions of the cuts is greater than an average of the cut widths at the intermediate portions of the cuts.

Clause 14. The embolic material delivery device of any of the preceding or following clauses, further comprising:

an inlet port operably connected to the axial lumen, wherein the embolic material delivery device is configured to receive the liquid embolic material via the inlet port; and an outlet port operably connected to the axial lumen, wherein the embolic material delivery device is configured to dispense the liquid embolic material via the outlet port, wherein the length of the conduit body between the inlet port and the outlet port is within a range of 140 to 200 cm.

Clause 15. The embolic material delivery device of any of the preceding or following clauses, wherein the conduit body further comprises an inner lubricious material between the hypotube and the axial lumen.

Clause 16. The embolic material delivery device of any of the preceding or following clauses, wherein the inner lubricious material comprises polytetrafluoroethylene, polyvinylidene fluoride, polyethylene, or a combination thereof.

Clause 17. The embolic material delivery device of any of the preceding or following clauses, wherein the conduit body further comprises an outer lubricious material extending around at least a portion of the jacket.

Clause 18. The embolic material delivery device of any of the preceding or following clauses, wherein the outer lubricious material comprises hyaluronic acid, polyvinylpyrrolidone, polyethylene oxide, or a combination thereof.

Clause 19. The embolic material delivery device of any of the preceding or following clauses, wherein:

the cuts individually define a cut length and a cut width perpendicular to the cut length; and an average of the cut widths at a distalmost portion of the conduit body is less than an average of the cut widths at a next distalmost portion of the conduit body.

Clause 20. The embolic material delivery device of any of the preceding or following clauses, wherein:

the distalmost portion of the conduit body extends along a distalmost 3% of the length of the conduit body;

the next distalmost portion of the conduit body extends along a next distalmost 10% of the length of the conduit body; and the average of the cut widths at the distalmost portion of the conduit body is at least 10% less than the average of the cut widths at the next distalmost portion of the conduit body.

Clause 21. The embolic material delivery device of any of the preceding or following clauses, wherein an average durometer of the jacket at a distalmost portion of the conduit body is less than an average durometer of the jacket at a next distalmost portion of the conduit body.

Clause 22. The embolic material delivery device of any of the preceding or following clauses, wherein:

the distalmost portion of the conduit body extends along a distalmost 3% of the length of the conduit body;

the next distalmost portion of the conduit body extends along a next distalmost 10% of the length of the conduit body; and the average durometer of the jacket at the distalmost portion of the conduit body is at least 10% less than the average durometer of the jacket at the next distalmost portion of the conduit body.

Clause 23. The embolic material delivery device of any of the preceding or following clauses, wherein:

the treatment location includes an intracranial aneurysm;

the embolic material delivery device further comprises an expandable structure carried by the conduit body; and the expandable structure is configured to be disposed at least partially within the intracranial aneurysm to reduce leakage of liquid embolic material from the intracranial aneurysm.

Clause 24. The embolic material delivery device of any of the preceding or following clauses, further comprising a detachment element through which the expandable structure is detachably connected to the conduit body, wherein the detachment element is configured to detach the expandable structure from the conduit body such that the conduit body can be withdrawn intravascularly away from the intracranial aneurysm while the expandable structure remains disposed at least partially within the intracranial aneurysm.

Clause 25. The embolic material delivery device of any of the preceding or following clauses, wherein:

the hypotube further comprises bridges interspersed between the cuts around the length of the conduit body;

the cuts and the bridges are longitudinally disposed along turns individually extending 360 degrees around the length of the conduit body; and the bridges at neighboring turns along the length of the conduit body are circumferentially offset from one another around the length of the conduit body.

Clause 26. The embolic material delivery device of any of the preceding or following clauses, wherein the bridges are cross-longitudinally disposed along a path extending helically around the length of the conduit body.

Clause 27. The embolic material delivery device of any of the preceding or following clauses, wherein neighboring turns along the length of the conduit body are spaced apart from one another.

Clause 28. The embolic material delivery device of any of the preceding or following clauses, wherein an average spacing between neighboring turns along the length of the conduit body at a distalmost portion of the conduit body is less than an average spacing between neighboring turns along the length of the conduit body at a next distalmost portion of the conduit body.

Clause 29. The embolic material delivery device of any of the preceding or following clauses, wherein:

the distalmost portion of the conduit body extends along a distalmost 3% of the length of the conduit body;

the next distalmost portion of the conduit body extends along a next distalmost 10% of the length of the conduit body; and the average spacing between the turns along the length of the conduit body at the distalmost portion of the conduit body is at least 10% less than the average spacing between the turns along the length of the conduit body at the next distalmost portion of the conduit body.

Clause 30. The embolic material delivery device of any of the preceding or following clauses, wherein the turns are longitudinally disposed along a path extending helically around the length of the conduit body.

Clause 31. The embolic material delivery device of any of the preceding or following clauses, wherein an average pitch of the path at a distalmost portion of the conduit body is less than an average pitch of the path at a next distalmost portion of the conduit body.

Clause 32. The embolic material delivery device of any of the preceding or following clauses, wherein:

the distalmost portion of the conduit body extends along a distalmost 3% of the length of the conduit body;

the next distalmost portion of the conduit body extends along a next distalmost 10% of the length of the conduit body; and the average pitch of the path at the distalmost portion of the conduit body is at least 10% less than the average pitch of the path at the next distalmost portion of the conduit body.

Clause 33. A method for treating an aneurysm at a neurovascular treatment location, the method comprising:

moving a distal end portion of a conduit body intravascularly toward the neurovascular treatment location, wherein the conduit body is elongate, defines an axial lumen, and includes a hypotube coaxially disposed around the axial lumen;

bending the conduit body while moving the distal end portion of a conduit body intravascularly toward the neurovascular treatment location, wherein bending the conduit body includes at least partially collapsing first cut regions of the hypotube and expanding second cut regions of the hypotube, and wherein the first and second cut regions are circumferentially opposite to one another around a length of the conduit body; and flowing liquid embolic material distally toward the aneurysm via the axial lumen after bending the conduit body and while at least a portion of the liquid embolic material is at a pressure of 9,000 psi or greater.

Clause 34. The method of any of the preceding or following clauses, wherein bending the conduit body includes:

compressing a first portion of an elastomeric jacket of the conduit body at the first cut regions; and stretching a second portion of the elastomeric jacket at the second cut regions.

Clause 35. The method of any of the preceding or following clauses, wherein flowing liquid embolic material distally toward the aneurysm via the axial lumen includes flowing liquid embolic material in direct contact with an inner lubricious material of the conduit body.

Clause 36. The method of any of the preceding or following clauses, further comprising:

flowing the liquid embolic material into the aneurysm; and

locating an expandable structure carried by the conduit body at least partially within the aneurysm to reduce leakage of the liquid embolic material from the aneurysm, wherein flowing the liquid embolic material into the aneurysm at least partially causes the expandable structure to transition from a first state toward a second state, and wherein the expandable structure occupies less space within the aneurysm in the second state than in the first state.

Clause 37. The method of any of the preceding or following clauses, further comprising:

detaching the expandable structure from the conduit body after transitioning the expandable structure from the first state toward the second state; and withdrawing the conduit body intravascularly away from the aneurysm while the expandable structure remains disposed at least partially within the aneurysm.

Clause 38. An embolic material delivery device, comprising:

a conduit body configured to extend intravascularly toward a treatment location, wherein the conduit body is elongate, defines an axial lumen, and comprises:

a proximal end portion, a distal end portion opposite to the proximal end portion along a length of the conduit body, wherein the axial lumen extends between the proximal and distal end portions of the conduit body, a hypotube comprising an outer surface and an inner surface coaxially disposed around the axial lumen, wherein the hypotube defines a wall thickness between the outer surface and the inner surface, and wherein the hypotube defines a plurality of cuts extending through the wall thickness, and a jacket extending around at least a portion of the outer surface of the hypotube and covering the plurality of cuts, wherein the conduit body is configured to convey liquid embolic material toward the treatment location via the axial lumen while at least a portion of the liquid embolic material is at a pressure of 9,000 psi or greater, and wherein the jacket is configured to fluidically seal the plurality of cuts such that at least a portion of the conduit body is configured to withstand the pressure of 9,000 psi or greater.

Clause 39. The embolic material delivery device of any of the preceding or following clauses, wherein the plurality of cuts comprise a plurality of slots, each slot comprising one or more sidewalls defined by the wall thickness of the hypotube.

Clause 40. The embolic material delivery device of any of the preceding or following clauses, wherein the conduit body defines an average wall thickness between an outer surface of the conduit body and an inner surface of the conduit body, and the average wall thickness is within a range of 0.004 to 0.008 inches.

Clause 41. The embolic material delivery device of any of the preceding or following clauses, wherein the jacket comprises a main portion and a plurality of protrusions connected to the main portion, and each protrusion extends at least partially into a respective cut to fluidically seal the respective cut such that the at least the portion of the conduit body is configured to withstand the pressure of 9,000 psi or greater.

Clause 42. The embolic material delivery device of any of the preceding or following clauses, wherein the hypotube comprises a first material defining a first elastic modulus, and the jacket comprises a second material defining a second elastic modulus less than the first elastic modulus to flexibly bridge the plurality of cuts.

Clause 43. The embolic material delivery device of any of the preceding or following clauses, wherein the second material of the jacket comprises a first composition at a first portion of the conduit body and a second composition at a second portion of the conduit body proximal to the first portion, and the second composition is different from the first composition such that the first portion of the conduit body comprises a greater flexibility than the second portion of the conduit body.

Clause 44. The embolic material delivery device of any of the preceding or following clauses, wherein:

the first material of the hypotube comprises stainless steel, nitinol, polyether ether ketone, or a combination thereof; and the second material of the jacket comprises polyurethane, poly(ether-amide), nylon, or a combination thereof.

Clause 45. The embolic material delivery device of any of the preceding or following clauses, wherein the length of the conduit body is within a range of 140 cm to 200 cm, and the conduit body is configured to withstand the pressure of 9,000 psi or greater along at least a portion of the length.

Clause 46. The embolic material delivery device of any of the preceding or following clauses, wherein the plurality of cuts are longitudinally disposed along a plurality of circumferential turns extending along the length of the conduit body.

Clause 47. The embolic material delivery device of any of the preceding or following clauses, wherein:

the hypotube further comprises a plurality of bridges, each bridge interspersed between a respective pair of cuts, and the plurality of cuts and the plurality of bridges are longitudinally disposed along the plurality of circumferential turns extending along the length of the conduit body.

Clause 48. The embolic material delivery device of any of the preceding or following clauses, wherein an average spacing between neighboring circumferential turns at a first portion of the conduit body is less than an average spacing between neighboring circumferential turns at a second portion of the conduit body proximal to the first portion, such that the first portion of the conduit body comprises a greater flexibility than the second portion of the conduit body.

Clause 49. The embolic material delivery device of any of the preceding or following clauses, wherein the pressure of 9,000 psi or greater is configured to cause the liquid embolic material to flow through the axial lumen at a flow rate of at least 0.05 mL/minute.

Clause 50. The embolic material delivery device of any of the preceding clauses or following clauses, wherein:

the treatment location includes an intracranial aneurysm, the embolic material delivery device further comprises an expandable structure carried by the conduit body, and the expandable structure is configured to be disposed at least partially within the intracranial aneurysm to reduce leakage of liquid embolic material from the intracranial aneurysm into a parent vessel of the intracranial aneurysm.

Clause 51. A method for treating an aneurysm at a neurovascular treatment location, the method comprising:

moving a distal end portion of a conduit body intravascularly toward the neurovascular treatment location, wherein the conduit body is elongate, defines an axial lumen, and comprises a hypotube coaxially disposed around the axial lumen, and wherein the hypotube comprises:

an outer surface, an inner surface coaxially disposed around the axial lumen, a first cut region defining a plurality of first cuts, each first cut extending from the outer surface to the inner surface, and a second cut region defining a plurality of second cuts, each second cut extending from the outer surface to the inner surface, wherein the second cut region is circumferentially opposite to the first cut region;

bending the conduit body by at least partially collapsing the plurality of first cuts of the first cut region of the hypotube and expanding the plurality of second cuts of the second cut region of the hypotube; and flowing liquid embolic material distally toward the aneurysm via the axial lumen, wherein at least a portion of the liquid embolic material is at a pressure of 9,000 psi or greater within the axial lumen.

Clause 52. The method of claim any of the preceding or following clauses, wherein the conduit body further comprises a jacket extending around at least a portion of the outer surface of the hypotube, the jacket comprising a first portion fluidically sealing the plurality of first cuts and second portion fluidically sealing the plurality of second cuts such that at least a portion of the conduit body is configured to withstand the pressure of 9,000 psi or greater.

Clause 53. The method of claim any of the preceding or following clauses, wherein bending the conduit body comprises:

compressing the first portion of the jacket to maintain fluidic sealing of the plurality of first cuts; and stretching the second portion of the jacket to maintain fluidic sealing of the plurality of second cuts.

Clause 54. The method of any of the preceding or following clauses, wherein flowing liquid embolic material distally toward the aneurysm via the axial lumen comprises flowing liquid embolic material in direct contact with an inner lubricious material of the conduit body.

Clause 55. The method of any of the preceding or following clauses, wherein flowing the liquid embolic material distally toward the aneurysm comprises pressurizing the at least the portion of the liquid embolic material to the pressure of 9,000 psi or greater to cause the liquid embolic material to flow at a flow rate of at least 0.05 mL/minute.

Clause 56. The method of any of the preceding or following clauses, further comprising:

flowing the liquid embolic material into the aneurysm; and locating an expandable structure carried by the conduit body at least partially within the aneurysm to reduce leakage of the liquid embolic material from the aneurysm and into a parent vessel of the aneurysm, wherein flowing the liquid embolic material into the aneurysm at least partially causes the expandable structure to transition from a first state toward a second state, and wherein the expandable structure occupies less space within the aneurysm in the second state than in the first state due to pressure of the liquid embolic material against the expandable structure.

Clause 57. The method of any of the preceding clauses, further comprising:

detaching the expandable structure from the conduit body after transitioning the expandable structure from the first state toward the second state, and withdrawing the conduit body intravascularly away from the aneurysm with the expandable structure disposed at least partially within the aneurysm.

BRIEF DESCRIPTION OF THE DRAWINGS

Many aspects of the present technology can be better understood with reference to the following drawings. The relative dimensions in the drawings may be to scale with respect to some embodiments of the present technology. With respect to other embodiments, the drawings may not be to scale. The drawings may also be enlarged arbitrarily. For clarity, reference-number labels for analogous components or features may be omitted when the appropriate reference-number labels for such analogous components or features are clear in the context of the specification and all of the drawings considered together. Furthermore, the same reference numbers may be used to identify analogous components or features in multiple described embodiments.

FIG. 1 is a profile view of an embolic material delivery device in accordance with at least some embodiments of the present technology.

FIG. 2 is a cross-sectional view of the embolic material delivery device shown in FIG. 1 taken along the line A-A in FIG. 1.

FIGS. 7-16 are cross-sectional views of the hypotube of the conduit body of the embolic material delivery device shown in FIG. 5 taken along lines C-C, D-D, E-E, F-F, G-G, H-H, J-J, K-K, M-M, and N-N, respectively, in FIG. 6B.

FIG. 17A is a profile view of a cut of a hypotube of a conduit body of an embolic material delivery device in accordance with at least some embodiments of the present technology.

FIG. 17B is an outline view of the cut shown in FIG. 17A.

FIG. 18 is a profile view of a hypotube of a conduit body of an embolic material delivery device in accordance with at least some embodiments of the present technology.

FIG. 19 is a profile view of a hypotube of a conduit body of an embolic material delivery device in accordance with at least some embodiments of the present technology.

DETAILED DESCRIPTION

Figures 3, 4A:
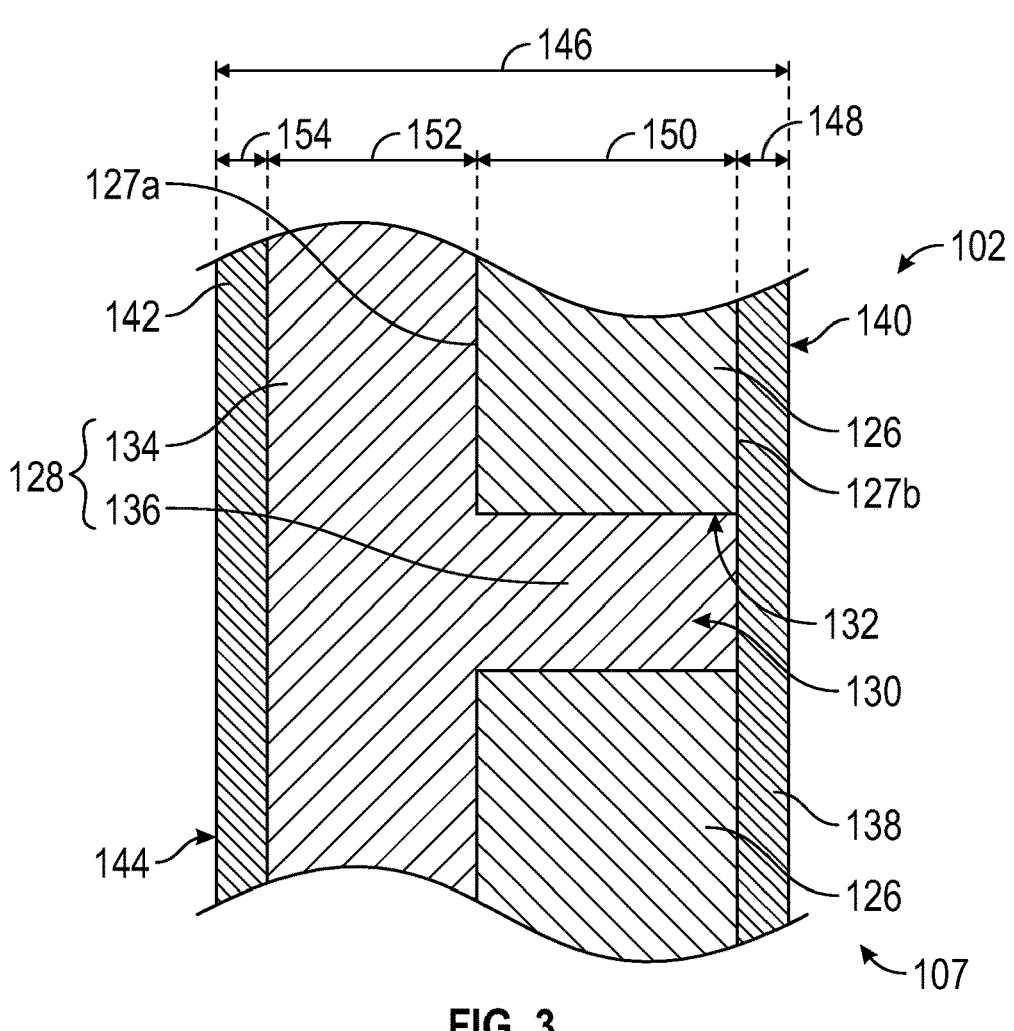
FIG. 3 is a cross-sectional view of a portion of a wall of a conduit body of the embolic material delivery device shown in FIG. 1.
FIG. 4A is a profile view of a hypotube of the conduit body of the embolic material delivery device shown in FIG. 1.

Disclosed herein are examples of embolic material delivery devices and related technology. As discussed above, treatment of an aneurysm can involve reducing blood flow within the aneurysm and thereby promoting thrombosis and embolization. One approach to reducing blood flow within an aneurysm includes introducing a liquid embolic material into the aneurysm. A conduit body can be advanced intravascularly to establish a flow channel between an extracorporeal inlet port and an outlet port within the aneurysm. Liquid embolic material can then be conveyed through this channel under pressure to reach the aneurysm. In at least some cases, the conduit body also carries an expandable structure that is also introduced into the aneurysm. As the liquid embolic material fills the aneurysm, the expandable structure can collapse against the neck of the aneurysm to reduce or prevent leakage of the liquid embolic material into the surrounding vasculature. Once the aneurysm is sufficiently filled, the conduit body can be detached from the expandable structure and removed.

One challenge associated with embolic material delivery devices is that liquid embolic material is often very viscous. High-viscosity liquid embolic material is advantageous for certain procedures because it tends to flow in a more controlled manner than low-viscosity liquid embolic material and/or for other reasons. The flow channel for delivery of liquid embolic material to an intracranial aneurysm, however, is typically long and narrow, such that achieving even a reasonable flow rate of high-viscosity liquid embolic material may involve the use of high pressures. The need to withstand these high pressures can limit the design and materials of conduit bodies of embolic material delivery devices in ways that are contrary to promoting other desirable functionality. For example, increasing the wall thickness of a conduit body may desirably increase the pressure rating of the conduit body, but may also undesirably increase the overall diameter of the conduit body and/or decrease the diameter of the flow channel within the conduit body. Moreover, increasing the wall thickness of a conduit body may increase the stiffness of the conduit body. Increased stiffness can have both desirable and undesirable consequences. Stiffer conduit bodies tend to be easier to push than more flexible conduit bodies. Stiffer conduit bodies, however, also tend to be less able than more flexible conduit bodies to move through tortuous anatomy.

Embolic material delivery devices in accordance with embodiments of the present technology at least partially address one or more of the foregoing challenges and/or other challenges associated with conventional technologies. In a particular example, an embolic material delivery device in accordance with at least some embodiments of the present technology includes a conduit body comprising a laser-cut hypotube and an elastomeric jacket. Together, these structures can provide both excellent pressure resistance and a relatively compact wall thickness. For example, to achieve a comparable pressure resistance, a conduit body including a metal braid rather than a laser-cut hypotube may require a wall thickness two or more times greater. Furthermore, hypotubes and jackets in accordance with at least some embodiments of the present technology have different features at different proximal-to-distal positions. Examples of these features include the density of the hypotube cuts, the width of the hypotube cuts, the arrangement of the hypotube cuts, the angle of the hypotube cuts, and the material of the jacket, among others. In this or another manner, the conduit body can be stiffer and more pressure resistant proximally, and more flexible and less pressure resistant distally, while having a consistent wall thickness. Pushability tends to be a more significant consideration at proximal portions of a conduit body than at distal portions of a conduit body. In contrast, flexibility tends to be a more significant consideration at distal portions of a conduit body than at proximal portions of a conduit body. Moreover, the pressure of liquid embolic material flowing through a conduit body decreases as the liquid embolic material moves distally such that pressure resistance tends to be more useful at proximal portions of a conduit body than at distal portions a conduit body. Other functional considerations that differ along a length of a conduit body are also possible.

Specific details of systems, devices, and methods in accordance with embodiments of the present technology are described herein with reference to FIGS. 1-26. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

FIG. 1 is a profile view of an embolic material delivery device 100 in accordance with at least some embodiments of the present technology. FIG. 2 is a cross-sectional view of the embolic material delivery device 100 taken along the line A-A in FIG. 1. With reference to FIGS. 1 and 2 together, the embolic material delivery device 100 can include an elongate conduit body 102 defining a length 103 and comprising a proximal end portion 104 and a distal end portion 106 opposite to one another along the length 103. In at least some embodiments, the length 103 is within a range of 120 to 220 cm, such as a range of 140 to 200 cm. The conduit body 102 can further define an axial lumen 107 extending between the proximal end portion 104 and the distal end portion 106. The embolic material delivery device 100 can be configured for treating an intracranial aneurysm. For example, the conduit body 102 can be configured to extend intravascularly toward a treatment location including an intracranial aneurysm and to convey liquid embolic material toward the treatment location via the axial lumen 107. As further discussed below, the conduit body 102 can have a relatively high pressure rating. For example, the conduit body 102 can be configured to convey liquid embolic material toward a treatment location including an intravascular aneurysm while at least a portion or the entirety of the liquid embolic material is at a pressure of 9,000 psi or greater, 11,000 psi or greater, and/or within a range of 9,000 to 20,000 psi. These high pressures can enable the liquid embolic material to be delivered through the conduit body 102 and to the treatment location at a flow rate of at least 0.05 mL/minute, 0.1 mL/minute, 0.15 mL/minute, 0.2 mL/minute, 0.25 mL/minute, 0.3 mL/minute, 0.35 mL/minute, 0.4 mL/minute, 0.45 mL/minute, or 0.5 mL/minute.

At the proximal end portion 104, the embolic material delivery device 100 can include a fitting 108 (e.g., a luer hub) configured to be attached to a source of liquid embolic material (not shown). The fitting 108 can be made of a material that is capable of withstanding the high pressures generated during delivery of the liquid embolic material, such as stainless steel (e.g., SS-304) or other light weight metal alloy. Also at the proximal end portion 104, the embolic material delivery device 100 can include an inlet port 109 operably connected to the axial lumen 107. The embolic material delivery device 100 can be configured to receive liquid embolic material via the inlet port 109. The embolic material delivery device 100 can further include an expandable structure 110 configured to be disposed at least partially within an intracranial aneurysm to reduce leakage of liquid embolic material from the intracranial aneurysm. The conduit body 102 can carry the expandable structure 110 at the distal end portion 106. Relatedly, the embolic material delivery device 100 can include a detachment element 112 through which the expandable structure 110 is detachably connected to the conduit body 102. The detachment element 112 can be coupled to the distal end portion 106 via a weld (not shown) or in another suitable manner.

In at least some cases, the detachment element 112 includes a first conduit 114 including a detachment zone 116 configured to be selectively severed. In this or another manner, the detachment element 112 can be configured to detach the expandable structure 110 from the conduit body 102 such that the conduit body 102 can be withdrawn intravascularly away from an intracranial aneurysm while the expandable structure 110 remains disposed at least partially within the intracranial aneurysm. In at least some cases, the detachment element 112 comprises an alloy (e.g., a nickel, cobalt, chromium, and molybdenum alloy) at the detachment zone 116 that melts or otherwise breaks in response to receiving an electrical current. In these and other cases, the detachment zone 116 can be electrically connected via the conduit body 102, a wire (not shown), or in another suitable manner to a controller (also not shown) configured to be extra-corporally positioned during a treatment procedure using the embolic material delivery device 100.

The expandable structure 110 can include a second conduit 118 extending distally from the first conduit 114. The outer diameter of the second conduit 118 can be smaller than the outer diameter of the first conduit 114 such that a proximal portion of the second conduit 118 can be securely nested within a distal portion of the first conduit 114. The expandable structure 110 can further include a mesh 120 fixedly connected proximally to the first conduit 114 and slidably connected distally to the second conduit 118. Together, the first and second conduits 114, 118 can define a channel 122 operably connected to the axial lumen 107. At a distal tip of the second conduit 118, the embolic material delivery device 100 can include an outlet port 124 operably connected to the axial lumen 107 via the channel 122. For example, the conduit body 102 can be configured to convey liquid embolic material distally toward the channel 122 via the axial lumen 107, the first and second conduits 114, 118 can be configured to convey the liquid embolic material distally toward the outlet port 124 via the channel 122, and the embolic material delivery device 100 can be configured to dispense the liquid embolic material into an intracranial aneurysm via the outlet port 124.

FIG. 3 is a cross-sectional view of a portion of a wall of the conduit body 102. The scale of FIG. 2 prevents accurate depiction of certain details of the wall. FIG. 3 is significantly enlarged to show these details. As shown in FIG. 3, the conduit body 102 can include a hypotube 126 coaxially disposed around the axial lumen 107. FIG. 4A is a profile view of the hypotube 126 in isolation. The hypotube 126 can include cuts 130 (e.g., slots, grooves, apertures, perforations, channels) configured to increase a flexibility of the conduit body 102 (e.g., relative to a conduit body including a hypotube defining equivalent dimensions as the hypotube 126 but with no cuts). As best seen in FIG. 3, the hypotube 126 can include an outer surface 127a and an inner surface 127b defining a wall thickness 150 of the hypotube 126, and the cuts 130 can extend through the wall thickness 150. Each cut 130 can include one or more cut surfaces 132 (e.g., sidewalls) defined by the wall thickness 150. The cut surfaces 132 can individually extend around a given one of the cuts 130. In the illustrated embodiment, the cut surfaces 132 are parallel surfaces, while in other embodiments, some or all of the cut surfaces 132 may be nonparallel surfaces such that the cut 130 is wider at the outer surface 127a than at the inner surface 127b, or vice-versa. At least some of the cuts 130 can be laser cuts (e.g., cuts formed by vaporizing or otherwise removing material with a laser). In addition or alternatively, at least some of the cuts 130 can be formed by waterjet erosion, plasma cutting, grinding, or another suitable subtractive process. As yet another alternative, the hypotube 126 can be formed with at least some of the cuts 130 by an additive process, such as 3D printing.

With reference to FIGS. 1-4A together, the conduit body 102 can include a jacket 128 extending around at least a portion of the hypotube 126. The jacket 128 can be disposed over at least a portion or the entirety of the outer surfaces 127a of the hypotube 126. The jacket 128 can cover the cuts 130 of the hypotube 126 to flexibly bridge the cuts 130. In the illustrated embodiment, the jacket 128 extends into and fills the cuts 130. For example, the jacket 128 can include a main portion 134 contacting the outer surface 127a of the hypotube 126, and a plurality of protrusions 136 extending inwardly from the main portion 134 at the cuts 130. Each protrusion 136 can extend from the outer surface 127a of the hypotube 126 toward the inner surface 127b of the hypotube 126, thereby partially or completely filling the respective cut 130. The main portion 134 and the protrusions 136 of the jacket 128 can be monolithic. Furthermore, the jacket 128 can be at least partially molded to conform to the shape of the cuts 130. For example, a tubular precursor of the jacket 128 can be installed over the hypotube 126 and subjected to heat and/or pressure to cause it to at least partially conform to the shape of the cuts 130. In other embodiments, at least some of the protrusions 136 can be absent and/or counterparts of at least some of the protrusions 136 can extend only partially into the cuts 130. In these and other cases, portions of the cuts 130 not entirely occupied by a material of the jacket 128 can instead be occupied by gas (e.g., air), an elastomeric material different than an elastomeric material of the jacket 128, and/or one or more other suitable structures separate from the jacket 128.

The conduit body 102 can be a composite structure in which the hypotube 126 and the jacket 128 provide complementary properties. For example, the hypotube 126 can serve at least primarily as a skeleton that structurally reinforces the conduit body 102. The jacket 128 can serve at least primarily as a flexible bridge across the cuts 130 such that the conduit body 102 can bend without kinking as it moves through tortuous anatomy. The jacket 128 can also fluidically seal the cuts 130 so the conduit body 102 can withstand the high pressures generated during delivery of the liquid embolic material through the axial lumen 107. The hypotube 126 and the jacket 128 can be made of different respective materials, with the material of the hypotube 126 being harder and/or stiffer than the material of the jacket 128. In some embodiments, for example, the hypotube 126 is made partially or entirely from a first material defining a first elastic modulus, and the jacket 128 is made partially or entirely from a second material defining a second elastic modulus. The second elastic modulus can be less than the first elastic modulus, such that the jacket 128 is more flexible and less stiff than the hypotube 126. For example, the first modulus can be at least $0.5 \times 10^6$ psi, $1 \times 10^6$ psi, $5 \times 10^6$ psi, $10 \times 10^6$ psi, or $20 \times 10^6$ psi; and the second modulus can be no more than $0.2 \times 10^6$ psi, $0.1 \times 10^6$ psi, $0.05 \times 10^6$ psi, $0.01 \times 10^6$ psi, $0.005 \times 10^6$ psi, or $0.001 \times 10^6$ psi. In at least some cases, the jacket 128 is elastomeric. In these and other cases, the hypotube 126 can be metal. Suitable materials for the hypotube 126 include stainless steel (e.g., 304 stainless steel), nitinol, engineered polymers (e.g., polyether ether ketone engineered polymers), and combinations thereof. Suitable materials for the jacket 128 include polyurethane, poly(ether-amide), nylon, and combinations thereof. In at least some cases, the jacket 128 defines an average durometer within a range of 20 D to 90 D.

With reference again to FIGS. 1-4A, the conduit body 102 can include an inner lubricious material 138 between the hypotube 126 and the axial lumen 107. For example, the inner lubricious material 138 can be directly adjacent to the axial lumen 107 at an inner surface 140 of the wall of the conduit body 102. In at least some cases, the inner lubricious material 138 is in contact with inner surface 127b of the hypotube 126 and/or with the protrusions 136 of the jacket 128. The inner lubricious material 138 can be useful, for example, to reduce friction between the wall of the conduit body 102 and liquid embolic material flowing through the axial lumen 107, thereby reducing a pressure drop of the conduit body 102. Suitable materials for the inner lubricious material 138 include polytetrafluoroethylene (e.g., ram-extruded or expanded and wrapped), polyvinylidene fluoride, polyethylene, and combinations thereof. The inner lubricious material 138 can be coated onto the hypotube 126, pre-formed and bonded (e.g., adhesively) to the hypotube 126, and/or applied to the hypotube 126 in another suitable manner. The conduit body 102 can further include an outer lubricious material 142 at an outer surface 144 of the wall of the conduit body 102. The outer lubricious material 142 can be useful, for example, to reduce friction between the wall of the conduit body 102 and a sheath (not shown), to increase a biocompatibility of the conduit body 102, and/or to reduce friction between the wall of the conduit body 102 and a wall of a body lumen. Suitable materials for the outer lubricious material 142 include hyaluronic acid, polyvinylpyrrolidone, polyethylene oxide, and combination thereof. Like the inner lubricious material 138, the outer lubricious material 142 can be coated onto the hypotube 126, pre-formed and bonded (e.g., adhesively) to the hypotube 126, and/or applied to the hypotube 126 in another suitable manner.

As shown in FIG. 3, the wall of the conduit body 102 can define an overall thickness 146. The inner lubricious material 138, the hypotube 126 excluding the cuts 130, the main portion 134 of the jacket 128, and the outer lubricious material 142 can define wall thicknesses 148, 150, 152, and 154, respectively. In at least some cases, the average overall thickness 146 of the wall of the conduit body 102 is within a range of 0.005 to 0.007 inches and/or within a range of 0.004 to 0.008 inches. In these and other cases, the average outer diameter of the conduit body 102 can be within a range of 0.028 to 0.030 inches and/or within a range of 0.02 to 0.04 inches. Furthermore, the average inner diameter of the conduit body 102 can be within a range of 0.015 to 0.019 inches and/or within a range of 0.010 to 0.024 inches. Furthermore, the average wall thickness 148 of the inner lubricious material 138 can be within a range of 0.0004 to 0.0008 inches and/or within a range of 0.0003 to 0.001 inches. Furthermore, the average wall thickness 150 of the hypotube 126 excluding the cuts 130 can be within a range of 0.0015 to 0.0035 inches and/or within a range of 0.001 to 0.005 inches. Furthermore, the average wall thickness 152 of the jacket 128 can be within a range of 0.0015 to 0.0025 inches, within a range of 0.001 to 0.004 inches, and/or no more than 110% of the average wall thickness 150 of the hypotube 126 excluding the cuts 130. Finally, the average thickness 154 of the outer lubricious material 142 can be within a range of 0.0004 to 0.0008 inches and/or within a range of 0.0003 to 0.001 inches.

As shown in FIG. 4A, the hypotube 126 can include bridges 155 interspersed between the cuts 130 around the length 103 of the conduit body 102. The cuts 130 and the bridges 155 can have different features at different portions of the hypotube 126. For example, the hypotube 126 can include a first portion 156, a second portion 158, a third portion 160, and a fourth portion 162 at successively more proximal positions along the length 103. The arrangement of the cuts 130 and the bridges 155 can be different between the first, second, third, and fourth portions 156, 158, 160, 162 of the hypotube 126 and consistent within the first, second, third, and fourth portions 156, 158, 160, 162 of the hypotube 126. In some cases, the first and second portions 156, 158 of the hypotube 126 together are longitudinally coextensive with a distalmost portion of the conduit body 102, such as a portion of the conduit body 102 extending along a distalmost 3% of the length 103. In these and other cases, the third and fourth portions 160, 162 of the hypotube 126 together can be longitudinally coextensive with a next distalmost portion of the conduit body 102, such as a portion of the conduit body 102 extending along a next distalmost 10% of the length 103. In other cases, counterparts of the first, second, third, and fourth portions 156, 158, 160, 162 of the hypotube 126 can have other suitable arrangements. Furthermore, a counterpart of the hypotube 126 can include more or fewer than four portions with different arrangements of cuts 130. For example, a counterpart of the hypotube 126 can have the same arrangement of cuts 130 throughout its length or have continuously varying arrangement of cuts 130 along its length.

Figures 4B, 5:
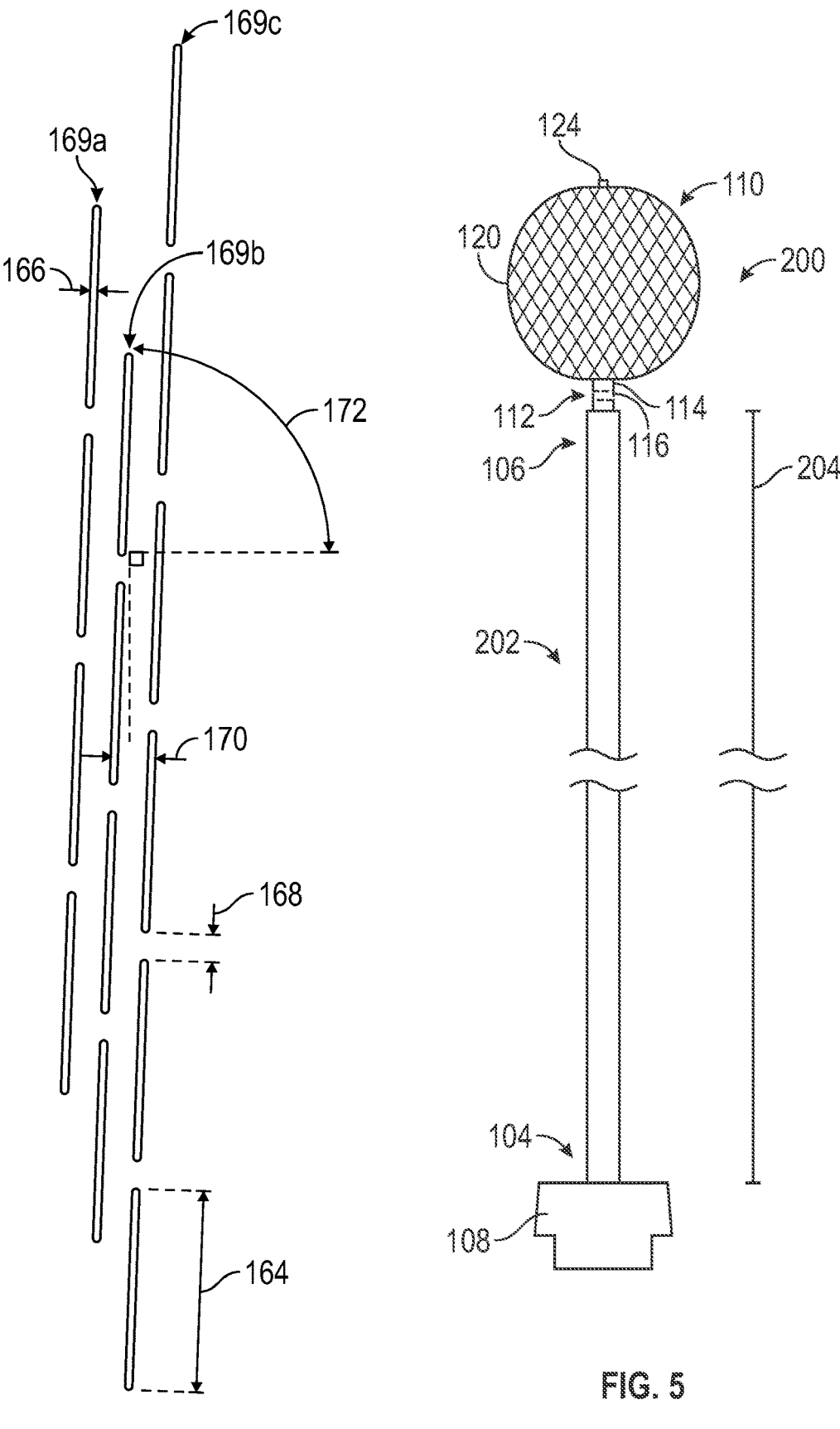
FIG. 4B is a flattened profile view of a pattern of cuts of the hypotube of the conduit body of the embolic material delivery device shown in FIG. 1.
FIG. 5 is a profile view of an embolic material delivery device in accordance with at least some embodiments of the present technology.

FIG. 4B is a flattened profile view of a pattern of the cuts 130 representative of the arrangements of the cuts 130 and the bridges 155 in the first, second, third, and fourth portions 156, 158, 160, 162 of the hypotube 126. As shown in FIG. 4B, the individual cuts 130 can define a cut length 164 and a cut width 166 perpendicular to the cut length 164. The individual bridges 155 can define a bridge length 168. The cuts 130 and the bridges 155 can be longitudinally disposed along a plurality of circumferential turns extending along the length 103 of the conduit body 102. Each turn can be defined by a set of cuts 130 and interspersed bridges 155 that collectively extend 360 degrees around the conduit body 102. For example, three turns 169a, 169b, and 169c are labeled in FIGS. 4A and 4B, with turns 169a and 169b being neighboring turns, and turns 169b and 169c being neighboring turns. The bridges 155 at neighboring turns along the length 103 can be circumferentially offset from one another around the length 103 of the conduit body 102. This can be useful, for example, to distribute bending forces on the hypotube 126, thereby strengthening the hypotube 126. In the illustrated embodiment, the turns are longitudinally disposed along a path extending helically around the length 103 of the conduit body 102. In other embodiments, as further discussed below, counterparts of the cuts 130 and the bridges 155 can be longitudinally disposed along turns spaced apart from one another along the length 103.

With reference again to FIGS. 4A and 4B, the path along which the turns are longitudinally disposed can define a pitch 170 and an angle 172. The pitch 170 and the angle 172 can be different between the first, second, third, and fourth portions 156, 158, 160, 162 of the hypotube 126. For example, the pitch 170 can be progressively greater and the angle 172 progressively smaller from the first portion 156 of the hypotube 126 toward the fourth portion 162 of the hypotube 126. The average pitch 170 at the distalmost portion of the conduit body 102 can be less than (e.g., at least 10% less than) the average pitch 170 at the next distalmost portion of the conduit body 102. This difference alone or together with other differences can cause a distalmost portion of the conduit body 102 to be more flexible than a next distalmost portion of the conduit body 102 without unduly sacrificing a pressure rating of the conduit body 102 given that a pressure of liquid embolic material flowing through the conduit body 102 tends to decrease as it moves distally.

In at least some cases, the cut widths 166 are relatively small. Removing less material at the cuts 130 can increase a pressure resistance of the conduit body 102 without unduly sacrificing flexibility. In the illustrated embodiment, the cut widths 166 are 0.038+/−0.005 mm. In other embodiments, counterparts of the cuts 130 can be wider or narrower. For example, an average of the cut widths 166 can be within a range of 0.028 to 0.043 mm and/or within a range of 0.020 to 0.030 mm. In addition or alternatively, a ratio of an average of the cut widths 166 to an average of the cut lengths 164 can be within a range of 0.020:1 to 0.028:1 and/or within a range of 0.015:1 to 0.022:1. Furthermore, counterparts of the cuts 130 at different portions of the length 103 can define different widths, which can cause the different portions to have different flexibilities. For example, counterparts of the cuts 130 at a distalmost 3% of the length 103 can define cut widths 166 with an average that is less than (e.g., at least 10% less than) an average of cut widths 166 defined by counterparts of the cuts 130 at a next distalmost 10% of the length 103. As another example, counterparts of the cuts 130 at a distalmost 3% of the length 103 can define cut widths 166 with an average that is greater than (e.g., at least 10% greater than) an average of cut widths 166 defined by counterparts of the cuts 130 at a next distalmost 10% of the length 103. Portions of the conduit body 102 with greater cut widths 166 can be more flexible than portions of the conduit body 102 with smaller cut widths 166.

Figures 6A, 6B:
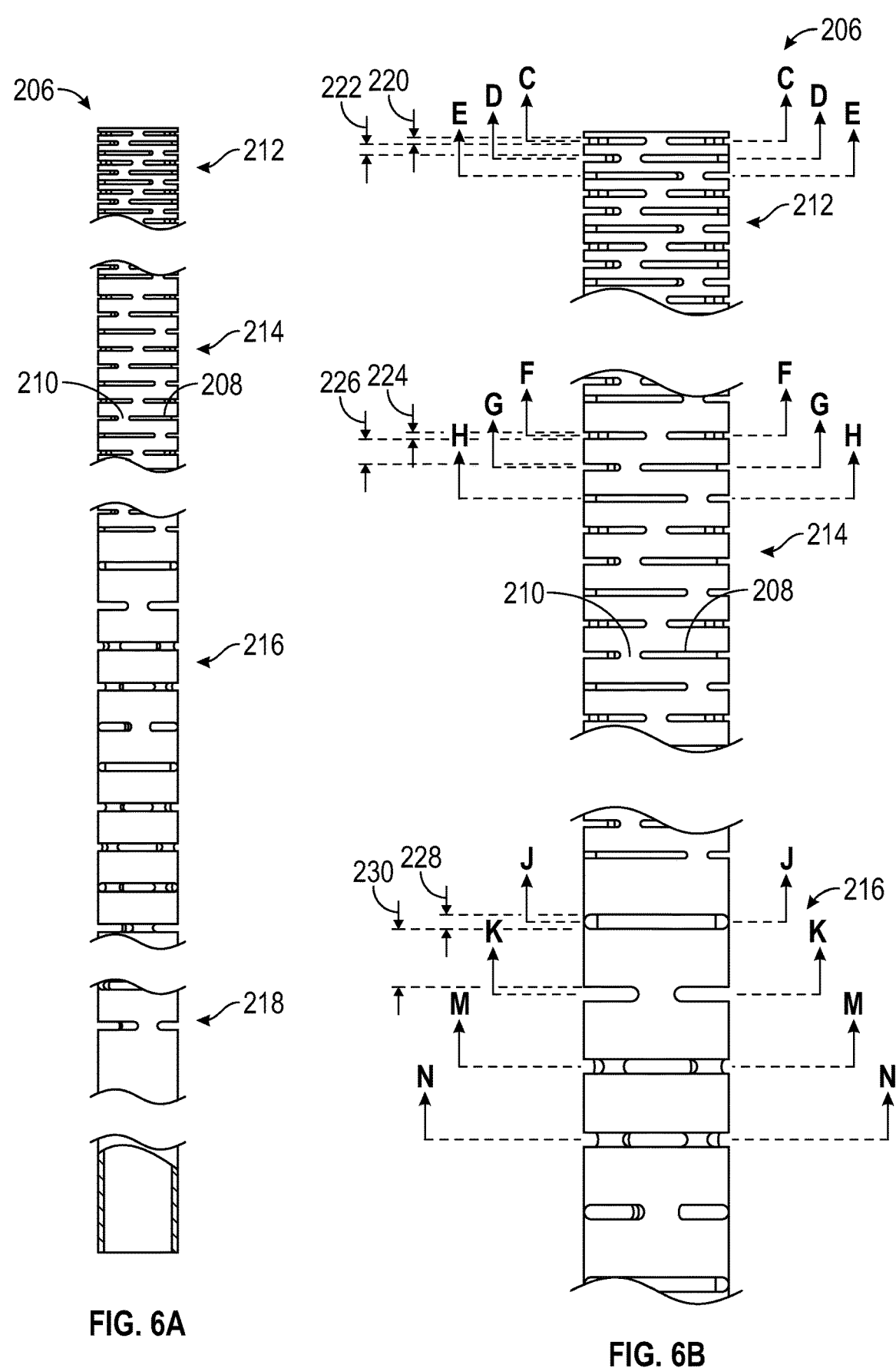
FIG. 6A is a profile view of a hypotube of a conduit body of the embolic material delivery device shown in FIG. 5.
FIG. 6B is an enlarged view of a portion of FIG. 6A.

FIG. 5 is a profile view of an embolic material delivery device 200 in accordance with at least some embodiments of the present technology. The embolic material delivery device 200 can include a conduit body 202 defining a length 204. The conduit body 202 can be similar to the conduit body 102 of the embolic material delivery device 100 described above, but with a different hypotube. FIG. 6A is a profile view of a hypotube 206 of the conduit body 202. FIG. 6B is an enlarged view of a portion of FIG. 6A. FIGS. 7-16 are cross-sectional views of the hypotube 206 taken along lines C-C, D-D, E-E, F-F, G-G, H-H, J-J, K-K, M-M, and N-N, respectively, in FIG. 6B. With reference to FIGS. 5-16 together, the hypotube 206 can include cuts 208 and bridges 210 interspersed with one another and longitudinally disposed along turns spaced apart from one another along the length 204. Similar to the hypotube 126, the hypotube 206 can include different longitudinal portions at which the cuts 208 have different features and/or arrangements. As shown in FIG. 6A, the hypotube 206 can include a first portion 212, a second portion 214, a third portion 216, and a fourth portion 218 at successively more proximal positions along the length 204.

The features and/or arrangements of the cuts 208 and the bridges 210 can be different between the first, second, third, and fourth portions 212, 214, 216, 218 of the hypotube 206 and consistent within the first, second, third, and fourth portions 212, 214, 216, 218 of the hypotube 206. In some cases, the first and second portions 212, 214 of the hypotube 206 together are longitudinally coextensive with a distalmost portion of the conduit body 202, such as a portion of the conduit body 202 extending along a distalmost 3% of the length 204. In these and other cases, the third portion 216 of the hypotube 206 can be longitudinally coextensive with a next distalmost portion of the conduit body 202, such as a portion of the conduit body 202 extending along a next distalmost 10% of the length 204. In other cases, counterparts of the first, second, third, and fourth portions 212, 214, 216, 218 of the hypotube 206 can have other suitable arrangements. Furthermore, a counterpart of the hypotube 206 can include more or fewer than four portions with different features and/or arrangements of cuts 208. For example, a counterpart of the hypotube 206 can have the same cuts 208 and/or arrangements of cuts 208 throughout its length or have continuously varying features and/or arrangements of cuts 208 along its length.

With reference again to FIGS. 5-16, the cuts 208 at the first portion 212 of the hypotube 206 can individually define a cut width 220 and can be longitudinally disposed with the bridges 210 along turns spaced apart from one another along the length 204 by a turn spacing 222. Similarly, the cuts 208 at the second portion 214 of the hypotube 206 can individually define a cut width 224 and can be longitudinally disposed with the bridges 210 along turns spaced apart from one another along the length 204 by a turn spacing 226. Also similarly, the cuts 208 at the third portion 216 of the hypotube 206 can individually define a cut width 228 and can be longitudinally disposed with the bridges 210 along turns spaced apart from one another along the length 204 by a turn spacing 230. The fourth portion 218 can be without cuts 208. As shown in FIG. 6B, an average of the cut widths 220, 224 can be less than (e.g., at least 10% less than) an average of the cut widths 228. Similarly, an average of the turn spacings 222, 226 can be less than (e.g., at least 10% less than) than an average of the turn spacings 230. As shown in FIGS. 7-16, the individual turns at the first and second portions 212, 214 of the hypotube 206 can include a greater number of the cuts 208 (e.g., one more, two more, etc.) than the individual turns at the third portion 216 of the hypotube 206. Moreover, the average circumferential length of the cuts 208 and of the bridges 210 around the length 204 of the conduit body 202 at the first and second portions 212, 214 of the hypotube 206 can be less than (e.g., at least 10% less than) the average circumferential length of the cuts 208 and of the bridges 210 around the length 204 of the conduit body 202 at the third portion 216 of the hypotube 206.

As with the pitch 170 of the cuts 130 discussed above with reference to the hypotube 126, the differences discussed above in the features and/or arrangements of the cuts 208 of the hypotube 206 between the first, second, and third portions 212, 214, 216 of the hypotube 206 can cause the hypotube 206 to have different properties at different positions along the length 204. For example, a distalmost portion of the conduit body 202 can be more flexible than a next distalmost portion of the conduit body 202 without unduly sacrificing a pressure rating and/or a pushability of the conduit body 202. With reference to FIGS. 1-16, other approaches to changing the properties of the conduit bodies 102, 202 at different positions along the lengths 103, 204 are also possible. For example, different portions of the jacket 128 can have different material compositions, e.g., some portions can be made of materials that have a lower elastic modulus and/or durometer than the materials of other portions. For instance, a composition of a counterpart of the jacket 128 at a distalmost portion of a counterpart of the conduit bodies 102, 202 can be different than at a next distalmost portion of the counterpart of the conduit bodies 102, 202. In these and other cases, an average durometer of a counterpart of the jacket 128 at a distalmost portion of a counterpart of the conduit bodies 102, 202 can be less than (e.g., at least 10% less than) an average durometer of the counterpart of the jacket 128 at a next distalmost portion of the counterpart of the conduit bodies 102, 202.

Counterparts of the cuts 130, 208 can have shapes and/or sizes other than those of the hypotubes 126, 206. FIGS. 17A and 17B, for example, illustrate an alternative cut shape. FIG. 17A is a profile view of a cut 300 of a hypotube of a conduit body of an embolic material delivery device in accordance with at least some embodiments of the present technology. FIG. 17B is an outline view of the cut 300. As shown in FIGS. 17A and 17B, the cut 300 can define a cut length 302 including a first end 304 and an opposite second end 306. The cut 300 can include a first end portion 308 at the first end 304 of the cut length 302, a second end portion 310 at the second end 306 of the cut length 302, and an intermediate portion 312 between the first and second end portions 308, 310. As shown in FIG. 17A, the cut 300 can be enlarged and rounded at the first and second end portions 308, 310. For example, an average width of the cut 300 can be greater (e.g., at least 10% greater) at the first and second end portions 308, 310 than at the intermediate portion 312. This shape can be useful, for example, to reduce or prevent the propagation of microcracks around the cut 300 that can result from bending a hypotube including the cut 300. Accordingly, the shape of the cut 300 can be applied to any of the cuts 130, 208 described above in various embodiments of the present technology.

Like the cuts 130, 208, the bridges 155, 210 can have features and/or arrangements that affect properties of the conduit bodies 102, 202. FIGS. 18 and 19 illustrate two examples of features and arrangements of counterparts of the bridges 155, 210. FIG. 18 is a profile view of a hypotube 350 that can be substituted for the hypotubes 126, 206 in various embodiments of the present technology. The hypotube 350 can include cuts 352, first bridges 354, and second bridges 356 longitudinally disposed along turns spaced apart from one another along a length of the hypotube 350. The first bridges 354 can be smaller than the second bridges 356. Furthermore, the first bridges 354 can be circumferentially aligned with one another and present at only some of the turns. The second bridges 356 can be circumferentially offset from one another incrementally from turn-to-turn and can likewise be present at only some of the turns. The second bridges 356 can be cross-longitudinally disposed along a path 358 extending helically around the length of the hypotube 400 and of a corresponding conduit body. The length, turn-to-turn circumferential offset, frequency, and/or other features of the second bridges 356 can be selected to change the shape of a cut-free portion of the hypotube 350 extending along the path 358. Where the cut-free portion of the hypotube 350 is larger, the hypotube 350 may be stiffer. In contrast, where the cut-free portion of the hypotube 350 is smaller, the hypotube 350 may be more flexible.

FIG. 19 is a profile view of another hypotube 400 that can be substituted for the hypotubes 126, 206 in various embodiments of the present technology. The hypotube 400 can include cuts 402 and bridges 404 longitudinally disposed along turns spaced apart from one another along a length of the hypotube 400. Unlike in the hypotube 350, the cuts 402 and bridges 404 of the hypotube 400 can be mostly consistent turn-to-turn, differing at least primarily with respect to their circumferential positions. The difference in the circumferential positions can cause the bridges 404 to be cross-longitudinally disposed along a path 406 extending helically around the length of the hypotube 400 and of a corresponding conduit body. The turn-to-turn circumferential offset of the bridges 404 can be selected to change the shape of a cut-free portion of the hypotube 400 extending along the path 406. Where a pitch of the path 406 is larger, the hypotube 400 may be stiffer. In contrast, wherein the pitch of the path 406 is smaller, the hypotube 400 may be more flexible.

Figure 20:
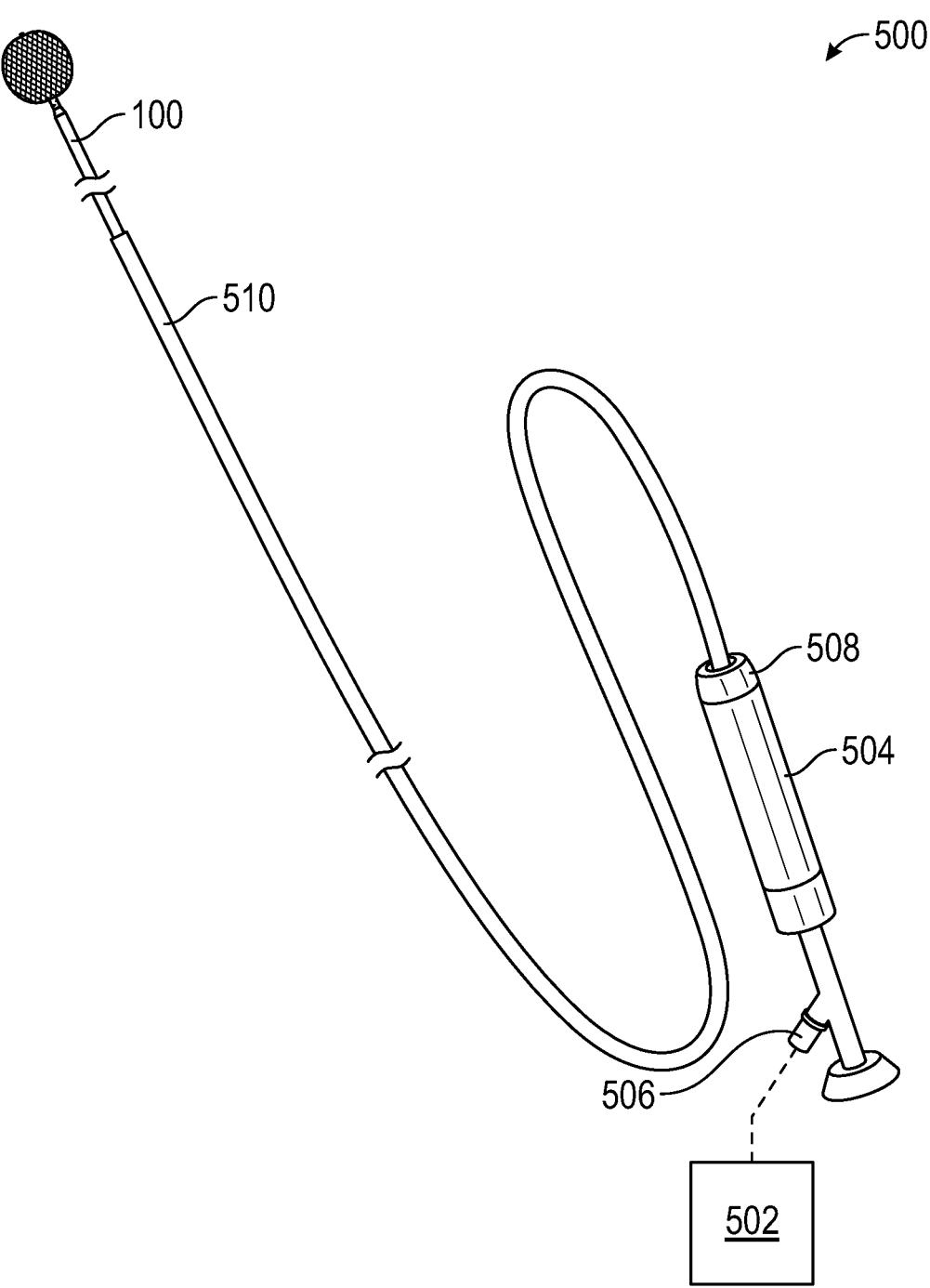
FIG. 20 is a perspective view of the embolic material delivery device shown in FIG. 1 and associated structures within a system in accordance with at least some embodiments of the present technology.

FIG. 20 is a perspective view of the embolic material delivery device 100 and associated structures within a system 500 for treating intracranial aneurysms in accordance with at least some embodiments of the present technology. With reference to FIGS. 1-20 together, the system 500 can include a liquid embolic material source 502 and a handle 504 having a port 506 through which the handle 504 is configured to receive liquid embolic material from the liquid embolic material source 502. The handle 504 can further include a cap 508 configured to capture the fitting 108. Extending distally from the handle 504, the system 500 can include an elongate sheath 510 slidably connected to the conduit body 102. The embolic material delivery device 100 can be movable relative to the sheath 510 and/or the sheath 510 can be movable relative to the conduit body 102. By this movement and/or in another suitable manner, the expandable structure 110 can be constrained in a low-profile delivery state within the sheath 510 during intravascular movement toward an aneurysm and unconstrained to resiliently expand into an expanded state within the aneurysm after the intravascular movement.

Figure 21A:
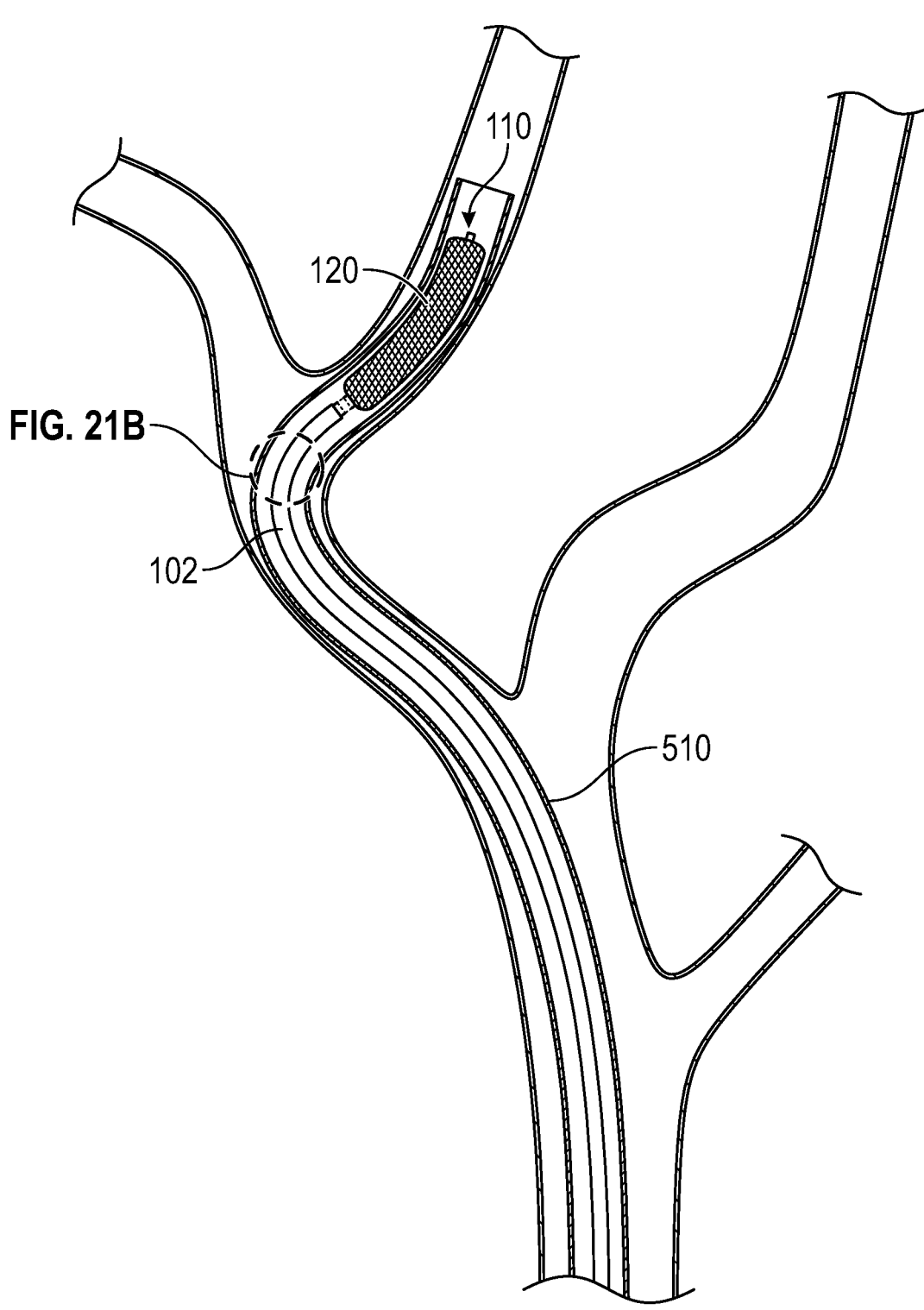
FIGS. 21A-25 are cross-sectional views of portions of the system shown in FIG. 20 and relevant anatomy at different respective times during a method for treating an aneurysm at a neurovascular treatment location in accordance with at least some embodiments of the present technology.
Figure 21B:
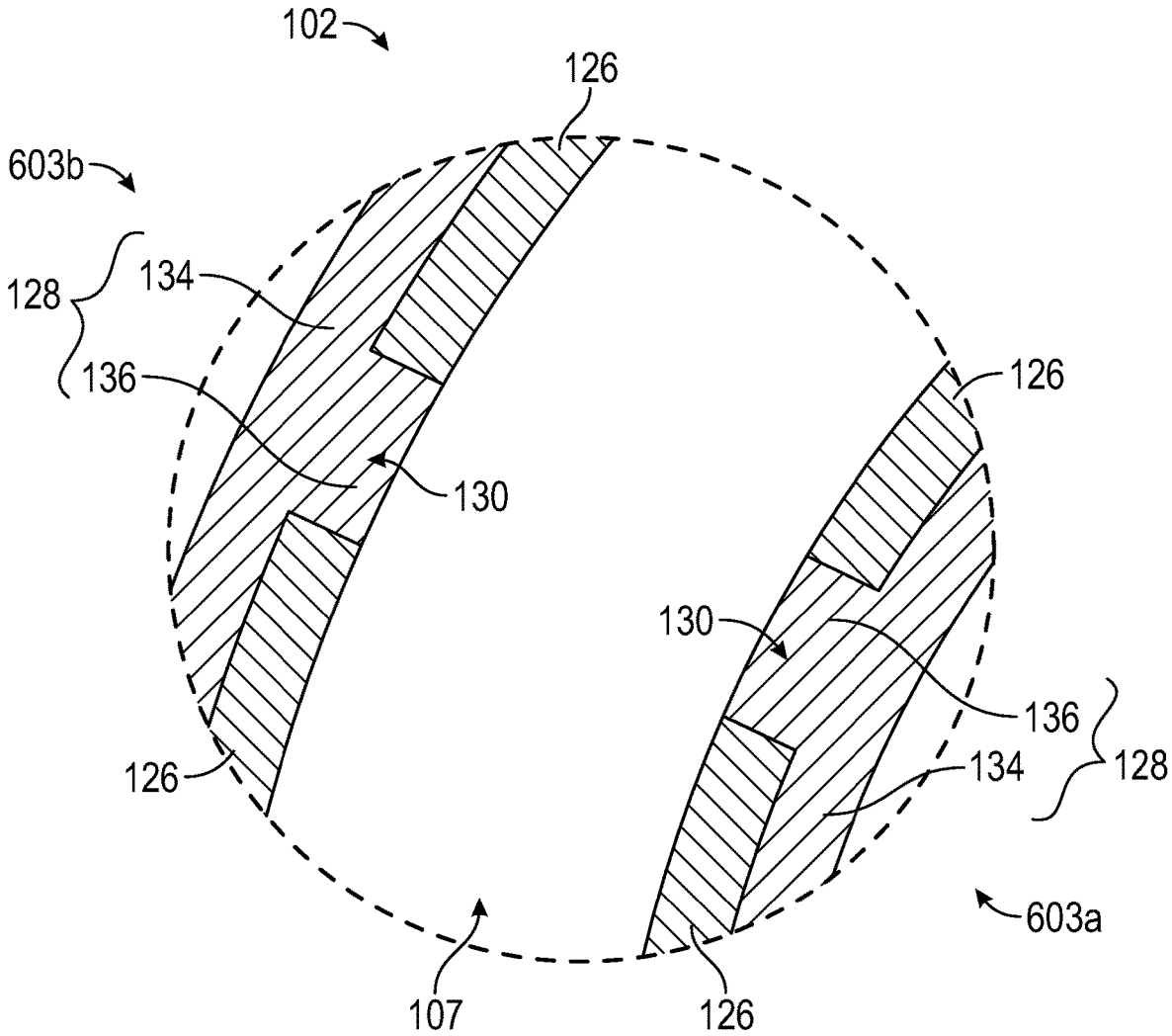

FIGS. 21A-25 are cross-sectional views of portions of the system 500 and relevant anatomy at different respective times during a method for treating an aneurysm 600 at a neurovascular treatment location 602 in accordance with at least some embodiments of the present technology. As shown in FIG. 21A, the method can include moving the distal end portion 106 intravascularly toward the neurovascular treatment location 602 while the expandable structure 110 is in the delivery state. During this movement, the method can include bending the conduit body 102. As shown in FIG. 21B (which is a closeup cross-sectional view of a portion of FIG. 21A), this can include at least partially collapsing one or more first cut regions 603a of the hypotube 126 and expanding one or more second cut regions 603b of the hypotube 126. The first cut regions 603a can include one or more cuts 130 at a first side of the conduit body 102 (e.g., the side closest to the center of curvature), while the second cut regions 603b can include one or more cuts 130 at a second side of the conduit body 102 circumferentially opposite to the first side (e.g., the side away from the center of curvature). The cuts 130 of the first cut region 603a can be compressed and/or collapsed by the bending of the hypotube 126, while the cuts 130 of the second cut regions 603b can be stretched and/or expanded by the bending of the hypotube 126. The method can further include compressing a first portion of the jacket 128 at the first cut regions 603a and stretching a second portion of the jacket 128 at the second cut regions 603b. For example, the protrusions 136 of the jacket 128 at the first cut regions 603a can be compressed and/or collapsed along with the cuts 130 of the first cut regions 603a, while the protrusions 136 of the jacket 128 at the second cut regions 603b can be stretched and/or expanded along with the cuts 130 of the second cut regions 603b. Accordingly, the jacket 128 can flexibly fill and bridge the cuts 130 of the first cut regions 603a and second cut regions 603b to maintain the fluidic sealing thereof.

Before, during, and/or after bending the conduit body 102, the method can include flowing liquid embolic material 604 distally toward the aneurysm 600 via the axial lumen 107. In at least some cases, the liquid embolic material 604 defines a viscosity greater than 30 centistokes. In these and other cases, at least a portion of the liquid embolic material 604 can be at a pressure of 9,000 psi or greater, 11,000 psi or greater, and/or within a range of 9,000 to 20,000 psi. Furthermore, at least some of the liquid embolic material 604 can be in direct contact with the inner lubricious material 138.

Figure 22:
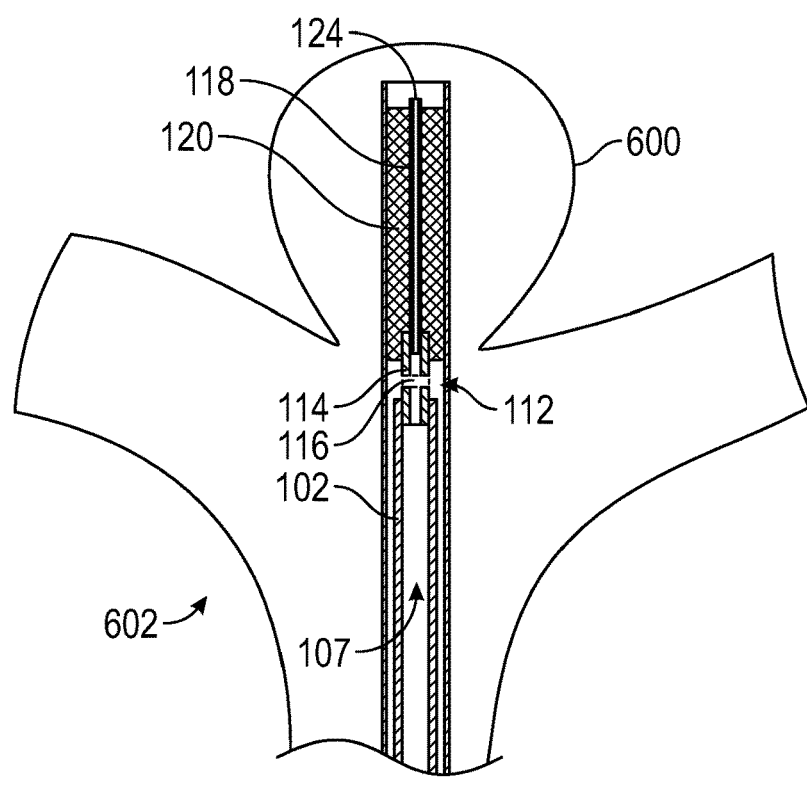
Figure 23:
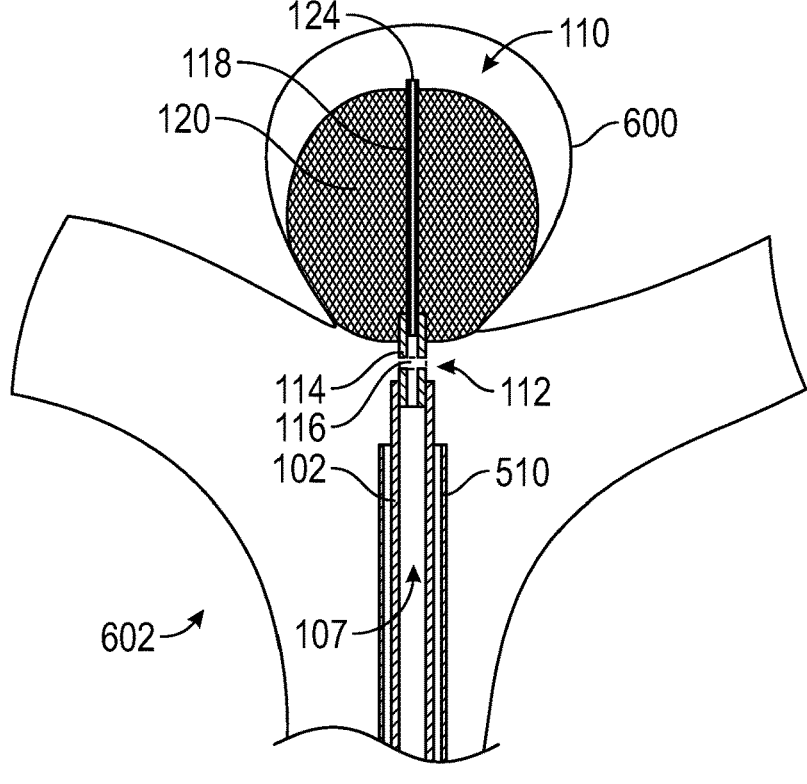
Figure 24:
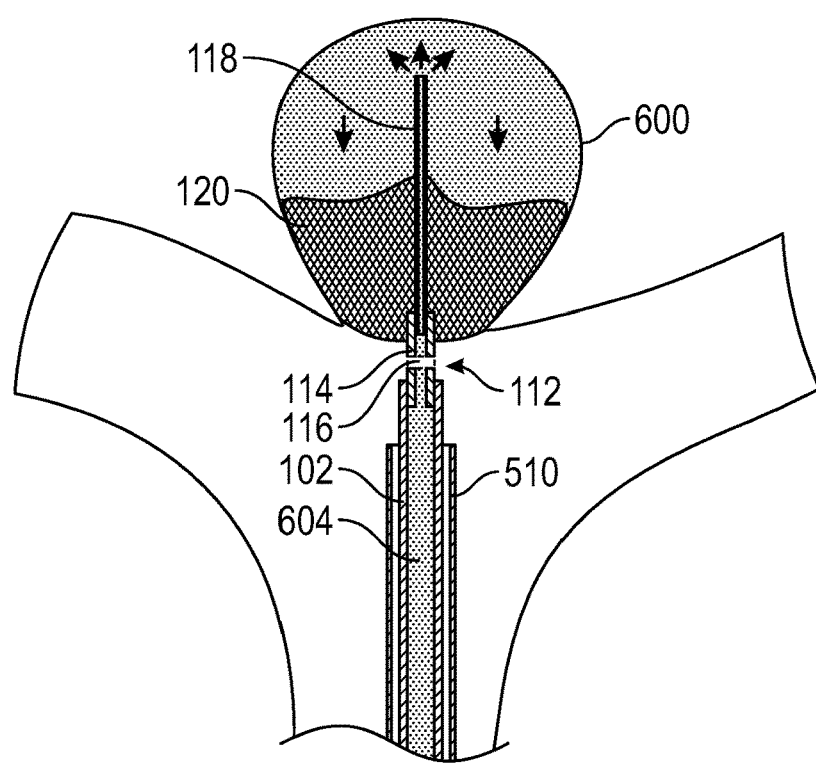
Figure 25:
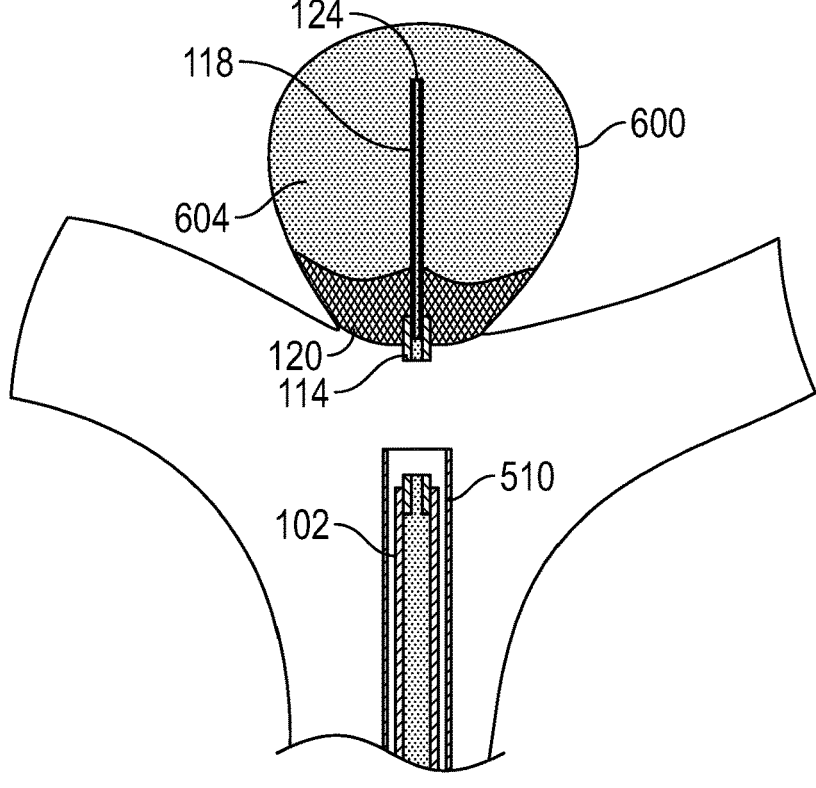

FIG. 22 shows portions of the system 500 after the distal end portion 106 reaches the neurovascular treatment location 602. The method can include locating the expandable structure 110 at least partially within the aneurysm 600. As shown in FIG. 23, the method can further include retracting the sheath 510 proximally to allow the expandable structure 110 to resiliently expand within the aneurysm 600. As shown in FIG. 24, the method can still further include flowing the liquid embolic material 604 distally within the axial lumen 107 and into the aneurysm 600. This can cause the expandable structure 110 to transition from the first state toward a second, more compact state. For example, pressure from the liquid embolic material 604 can cause the expandable structure 110 to collapse against a neck of the aneurysm 600 and thereby reduce or prevent leakage of the liquid embolic material 604 from the aneurysm 600. As shown in FIG. 25, when the aneurysm 600 is sufficiently filled, the detachment element 112 can be activated causing it to sever at the detachment zone 116. The conduit body 102 can then be retracted proximally into the sheath 510. The conduit body 102 and the sheath 510 can then be removed from the vasculature.

Experimental Example: Pressure Testing

A conduit body of an embolic material delivery device in accordance with at least some embodiments of the present technology was pressure tested. The tested conduit body shared certain features with the conduit body 102 described above with reference to FIGS. 1-4B. Accordingly, FIGS. 1-4B may be cited to describe aspects of the tested conduit body with the understanding that the tested conduit body may not correspond exactly to the conduit body 102. In the tested conduit body, the jacket 128 was made of PEXBAR® tubing laminated together. The inner lubricious material 138 was a tube liner made of an ultra-thin expanded polytet-rafluoroethylene tape (thickness less than 0.001 inches). The tape was wrapped with a winder at an angle on a silver-plated copper mandrel, then stretched and removed from the mandrel to form the tube liner. The hypotube 126 was made of 304 stainless steel. The tested conduit body had an inner diameter of 0.017 inches, an outer diameter within a range of 0.028 to 0.030 inches, and a total length of 168 cm with a working length of 165 cm. The cut lengths 164 were consistent among the cuts 130 at 1.600 mm. The cut widths 166 were consistent among the cuts 130 at 0.038+/−0.005 mm. The bridge lengths 168, the pitch 170, and the angle 172 varied at different portions of the length 103 as indicated in Table 1 below.

TABLE 1

| Arrangement of Cuts in Tested Hypotube | | | |
| --- | --- | --- | --- |
| Distance Range (mm) from Distalmost End | Bridge Length (mm) | Pitch (mm) | Angle (degrees) |
| 0-0.200 | n/a | n/a | n/a |
| 0.200-40.00 | 0.230 | 0.296 | 88.0 |
| 40.00-100.00 | 0.250 | 0.370 | 87.5 |
| 100.00-200.00 | 0.270 | 0.445 | 87.0 |
| 200.00-400.00 | 0.290 | 0.5195 | 86.5 |
| 400.00-950.00 | 0.330 | 0.668 | 85.5 |

Figure 26:
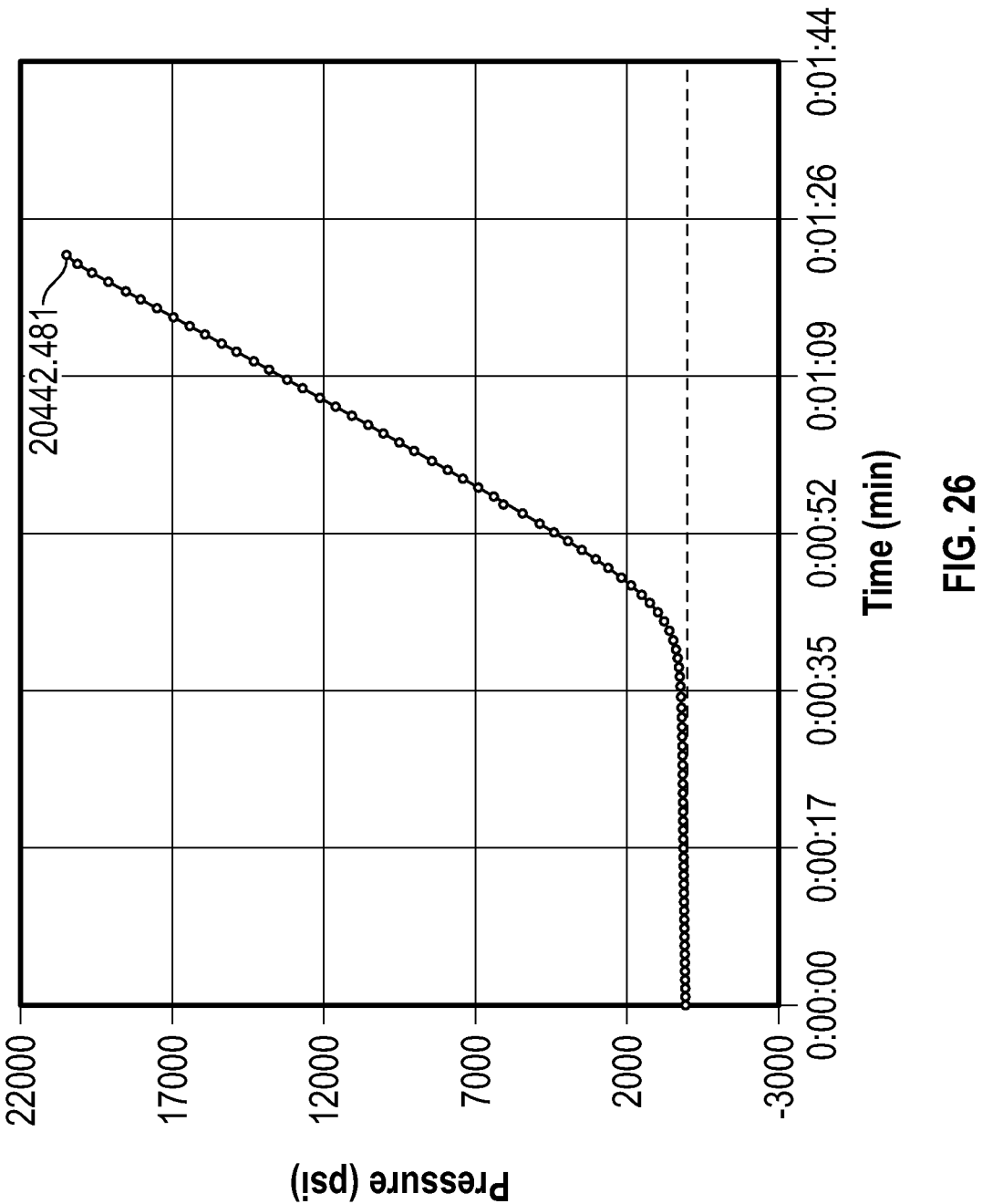
FIG. 26 is a plot of pressure versus time for a pressure test of a conduit body of an embolic material delivery device in accordance with at least some embodiments of the present technology.

In the experiment, a viscous, chitosan-based liquid medium was injected through a proximal luer hub via a high-pressure stainless steel syringe. The distal tip of the tested conduit body was clamped with a hemostat to prevent the medium from escaping. The pressure of the medium was increased and monitored. FIG. 26 is a plot of the pressure of the medium versus time. In FIG. 26, the linear increase in the plot indicates an absence of bursting or leakage. As shown in FIG. 26, the tested conduit body maintained its structural integrity up to pressures over 20,000 psi.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may be disclosed herein in the context of those embodiments, other embodiments may also exhibit such advantages, and not all embodiments need necessarily exhibit such advantages or other advantages disclosed herein to fall within the scope of the present technology. This disclosure and the associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising." "including." and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various structures. It should be understood that such terms do not denote absolute orientation. The words "helix," "helical," and the like as used herein do not require that the corresponding structure be a geometrically precise helix, but rather that the structure resembles a helix or that a person of ordinary skill in the art would otherwise recognize the structure to have helical characteristics. Furthermore, reference herein to "one embodiment," "an embodiment," or similar phrases means that a particular feature, structure, operation, or characteristic described in connection with such phrases can be included in at least one embodiment of the present technology. Thus, such phrases as used herein are not necessarily all referring to the same embodiment. Finally, it should be noted that various particular features, structures, operations, and characteristics of the embodiments described herein may be combined in any suitable manner in additional embodiments in accordance with the present technology.

We claim:

1. An embolic material delivery device, comprising:
a conduit body configured to extend intravascularly toward a treatment location, wherein the conduit body is elongate, defines an axial lumen, and comprises:
a proximal end portion,
a distal end portion opposite to the proximal end portion along a length of the conduit body, wherein the axial lumen extends between the proximal and distal end portions of the conduit body along a longitudinal axis of the conduit body,
a hypotube comprising an outer surface and an inner surface coaxially disposed around the axial lumen, wherein the hypotube defines a wall thickness between the outer surface and the inner surface, wherein the hypotube defines a plurality of cuts and a plurality of bridges, each bridge interspersed between a respective pair of cuts, wherein the plurality of cuts and the plurality of bridges are circumferentially disposed along a plurality of circumferential turns extending along the length of the conduit body, wherein each bridge has a respective bridge length along at least one of the plurality of circumferential turns between the respective pair of cuts, wherein the plurality of cuts extend through the wall thickness with each cut extending at least partially circumferentially around the hypotube along a respective cut axis, wherein an angle between the cut axis and the longitudinal axis is progressively less orthogonal from the distal end portion of the conduit body to the proximal end portion of the conduit body, and wherein the bridge length increases as the angle decreases, and a jacket extending around at least a portion of the outer surface of the hypotube and covering the plurality of cuts, wherein the conduit body is configured to convey liquid embolic material toward the treatment location via the axial lumen while at least a portion of the liquid embolic material is at a pressure of 9,000 psi or greater, and wherein the jacket is configured to fluidically seal the plurality of cuts such that at least a portion of the conduit body is configured to withstand the pressure of 9,000 psi or greater.

2. The embolic material delivery device of claim 1, wherein the plurality of cuts comprise a plurality of slots, each slot comprising one or more sidewalls defined by the wall thickness of the hypotube.

3. The embolic material delivery device of claim 1, wherein the conduit body defines an average wall thickness between an outer surface of the conduit body and an inner surface of the conduit body, and the average wall thickness is within a range of 0.004 to 0.008 inches.

4. The embolic material delivery device of claim 1, wherein the jacket comprises a main portion and a plurality of protrusions connected to the main portion, and each protrusion extends at least partially into a respective cut to fluidically seal the respective cut such that at least the portion of the conduit body is configured to withstand the pressure of 9,000 psi or greater.

5. The embolic material delivery device of claim 1, wherein the hypotube comprises a first material defining a first elastic modulus, and the jacket comprises a second material defining a second elastic modulus less than the first elastic modulus to flexibly bridge the plurality of cuts.

6. The embolic material delivery device of claim 5, wherein the second material of the jacket comprises a first composition at a first portion of the conduit body and a second composition at a second portion of the conduit body proximal to the first portion, and the second composition is different from the first composition such that the first portion of the conduit body comprises a greater flexibility than the second portion of the conduit body.

7. The embolic material delivery device of claim 5, wherein:

the first material of the hypotube comprises stainless steel, nitinol, polyether ether ketone, or a combination thereof; and the second material of the jacket comprises polyurethane, poly (ether-amide), nylon, or a combination thereof.

8. The embolic material delivery device of claim 1, wherein the length of the conduit body is within a range of 140 cm to 200 cm, and the conduit body is configured to withstand the pressure of 9,000 psi or greater along at least a portion of the length.

9. The embolic material delivery device of claim 1, wherein an average spacing between neighboring circumferential turns at a first portion of the conduit body is less than an average spacing between neighboring circumferential turns at a second portion of the conduit body proximal to the first portion, such that the first portion of the conduit body comprises a greater flexibility than the second portion of the conduit body.

10. The embolic material delivery device of claim 1, wherein the pressure of 9,000 psi or greater is configured to cause the liquid embolic material to flow through the axial lumen at a flow rate of at least 0.05 mL/minute.

11. The embolic material delivery device of claim 1, wherein:

the treatment location includes an intracranial aneurysm, the embolic material delivery device further comprises an expandable structure carried by the conduit body, and the expandable structure is configured to be disposed at least partially within the intracranial aneurysm to reduce leakage of liquid embolic material from the intracranial aneurysm into a parent vessel of the intracranial aneurysm.

12. The embolic material delivery device of claim 1, wherein each cut has a respective cut length along at least one of the plurality of circumferential turns, where cut lengths for the plurality of cuts are equal.

13. An embolic material delivery device, comprising:

a conduit body configured to extend intravascularly toward a treatment location, wherein the conduit body is elongate, defines an axial lumen, and comprises:

a proximal end portion, a distal end portion opposite to the proximal end portion along a length of the conduit body, wherein the axial lumen extends between the proximal and distal end portions of the conduit body along a longitudinal axis of the conduit body, a hypotube comprising an outer surface and an inner surface coaxially disposed around the axial lumen, wherein the hypotube defines a wall thickness between the outer surface and the inner surface, wherein the hypotube defines a plurality of cuts and a plurality of bridges, each bridge interspersed between a respective pair of cuts, wherein the plurality of cuts and the plurality of bridges are disposed along a plurality of circumferential turns extending along the length of the conduit body, wherein the plurality of cuts extend through the wall thickness with each cut extending at least partially circumferentially around the hypotube along a respective cut axis, and wherein an angle between the cut axis and the longitudinal axis is progressively less orthogonal from the distal end portion of the conduit body to the proximal end portion of the conduit body, and a jacket extending around at least a portion of the outer surface of the hypotube and covering the plurality of cuts, wherein each bridge has a respective bridge length measured circumferentially around the hypotube along at least one of the plurality of circumferential turns between the respective pair of cuts, the bridge length increasing from the distal end portion of the conduit body to the proximal end portion of the conduit body, and wherein each cut has a respective cut length along at least one of the plurality of circumferential turns, wherein the cut length is constant from the distal end portion of the conduit body to the proximal end portion of the conduit body.

* * * * *